US008846017B2

(12) United States Patent  
Biganska et al.

(10) Patent No.: US 8,846,017 B2  
(45) Date of Patent: Sep. 30, 2014

(54) COSMETIC COMPOSITIONS COMPRISING AT LEAST ONE CATIONIC COPOLYMER AND AT LEAST ONE AMINO SILICONE AND METHODS OF USE THEREOF

(75) Inventors: Olga Biganska, Asnières sur Seine (FR); Laurent Chesneau, Levallois Perret (FR)

(73) Assignee: L'Oreal, Paris (FR)

( * ) Notice: Subject to any disclaimer, the term of this patent is extended or adjusted under 35 U.S.C. 154(b) by 607 days.

(21) Appl. No.: 12/210,642

(22) Filed: Sep. 15, 2008

(65) Prior Publication Data

US 2009/0074699 A1    Mar. 19, 2009

Related U.S. Application Data

(60) Provisional application No. 60/960,279, filed on Sep. 24, 2007.

(30) Foreign Application Priority Data

Sep. 14, 2007    (FR) ..................... 07 57566

(51) Int. Cl.
| | |
|---|---|
| *A61Q 5/12* | (2006.01) |
| *A61K 8/898* | (2006.01) |
| *A61Q 5/02* | (2006.01) |
| *A61K 8/81* | (2006.01) |
| *A61K 8/86* | (2006.01) |

(52) U.S. Cl.  
CPC .. *A61Q 5/02* (2013.01); *A61Q 5/12* (2013.01); *A61K 8/898* (2013.01); *A61K 2800/5426* (2013.01); *A61K 8/8152* (2013.01); *A61K 2800/594* (2013.01); *A61K 8/86* (2013.01)  
USPC ..................................................... 424/70.12

(58) Field of Classification Search  
None  
See application file for complete search history.

(56) References Cited

U.S. PATENT DOCUMENTS

| 6,383,994 | B1 | 5/2002 | Maurin et al. | |
|---|---|---|---|---|
| 2003/0147842 | A1 | 8/2003 | Restle et al. | |
| 2004/0010863 | A1* | 1/2004 | Gawtrey et al. | 8/405 |
| 2004/0241130 | A1* | 12/2004 | Tamareselvy et al. | 424/70.16 |
| 2005/0169864 | A1* | 8/2005 | Derici et al. | 424/70.11 |

FOREIGN PATENT DOCUMENTS

| FR | 2 798 852 | 3/2001 |
|---|---|---|
| FR | 2 831 800 | 5/2003 |
| WO | WO 2005/092276 | 10/2005 |

OTHER PUBLICATIONS

Lubrizol, "Deep Conditioner for Ethnic Hair," Sep. 13, 2007, pp. 1-2.*  
Lubrizol, "SilSense Q-Plus Silicone," Jun. 2005, pp. 1-3.*  
Park et al., Cosmetic Science Technology, 2006, pp. 241-248.*  
"Carbopol Aqua SF-1 Polymer: Product Summary Sheet," 2002, pp. 1-2.*  
Anonymous, "Deep Conditioner for Ethnic Hair," dated Sep. 13, 2007, pulled from www.personalcare.noveon.com/formulas/E-0018.pdf, on Apr. 16, 2008.  
Anonymous, "Hair Conditioning Mask," dated Oct. 30, 2007, pulled from www.personalcare.noveon.com/formulas/CD-0016.pdf, on Apr. 21, 2008.  
Anonymous, "Silsense A-21 & A-23 Silicones: Amino Functional Silicones," dated Jun. 27, 2005, pulled from www.personalcare.noveon.com/technicaldatasheets/TDS-321_silsense_A-21_A-23.pdf, on Apr. 16, 2008.  
Park, A. et al., "Carbopol Aqua CC Polymer: The Premier Cationic Compatible Rheology Modifier for Low pH Formulations," Cosmetic Science Technology, Nov. 14, 2006, pp. 241-247.  
French Search Report for FR 07/57566, dated Apr. 22, 2008.

* cited by examiner

*Primary Examiner* — Brian Gulledge  
(74) *Attorney, Agent, or Firm* — The Marbury Law Group, PLLC

(57) ABSTRACT

The present disclosure relates to novel cosmetic compositions comprising, in a cosmetically acceptable medium:
 (i)—at least one cationic polymer produced by polymerization of a monomer mixture comprising:
  a) at least one vinyl monomer substituted with at least one amino group,
  b) at least one hydrophobic nonionic vinyl monomer, and
  c) at least one associative vinyl monomer, and
  e) at least one hydroxylated nonionic vinyl monomer, and
 (ii)—at least one amino silicone chosen from
  a) amino silicones comprising at least one primary amine function of formula (VI):

$$R-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_n-\left[O-\underset{\underset{\underset{\underset{\underset{NH_2}{|}}{B}}{|}}{\underset{NH}{|}}}{\overset{\overset{R'}{|}}{Si}}\right]_m-O-\underset{\underset{CH_3}{|}}{\overset{\overset{CH_3}{|}}{Si}}-R'' \quad (VI)$$

wherein R, R', and R", which may be identical or different, are chosen from $C_1$-$C_4$ alkyl radicals, $C_1$-$C_4$ alkoxy radicals, and OH; A and B are independently chosen from linear and branched $C_2$-$C_8$ alkylene radicals,  
 with the proviso that R and R" are not simultaneously hydroxyl groups,  
 A is chosen from $C_3$-$C_6$ alkylene radicals; B is chosen from $C_2$-$C_4$ alkylene radicals; and  
 m and n are integers that depend on the molecular weight and whose sum ranges from 1 to 2000,  
 and  
  b) non-amidated amino silicones comprising at least one quaternized amine function.  
These compositions may be used for washing and/or conditioning keratin materials such as the hair or the skin.

23 Claims, No Drawings

COSMETIC COMPOSITIONS COMPRISING AT LEAST ONE CATIONIC COPOLYMER AND AT LEAST ONE AMINO SILICONE AND METHODS OF USE THEREOF

This application claims benefit of U.S. Provisional Application No. 60/960,279, filed Sep. 24, 2007, the contents of which are incorporated herein by reference. This application also claims benefit of priority under 35 U.S.C. §119 to French Patent Application No. FR 0757566, filed Sep. 14, 2007, the contents of which are also incorporated herein by reference.

The present disclosure relates to novel cosmetic compositions comprising, in a cosmetically acceptable medium, at least one amino silicone and at least one cationic copolymer.

It is well known that hair which has been sensitized (i.e., damaged and/or embrittled) to varying degrees by the action of atmospheric agents or the action of mechanical or chemical treatments, such as dyes, bleaches, and/or permanent-waving, is often difficult to disentangle and to style, and lacks softness.

It is known to use conditioners, for example, cationic and amphoteric polymers or silicones, in compositions for washing or caring for keratin materials such as the hair, in order to disentangle the hair and to give it softness and flexibility. However, these polymers or silicones may have the disadvantage of lankness of the hairstyle (lack of lightness of the hair) and lack of smoothness (hair not uniform from the root to the end) on dried hair.

In addition, the use of cationic or amphoteric polymers for this purpose has other drawbacks. On account of their high affinity for the hair, some of these polymers become deposited thereon to a large extent during repeated use, and lead to adverse effects such as an unpleasant, laden feel, stiffening of the hair, and interfiber adhesion which has an effect on styling. These drawbacks are accentuated in the case of fine hair, which lacks liveliness and body.

It is also known in the hair field to use amino silicones in shampoo compositions as conditioning agents for improving the softness, feel and disentangling of the hair. However, it has been found that these silicones lead to the formation of an unattractive layer at the surface of the shampoo, which is harmful to the performance of the shampoo. To avoid the appearance of this phenomenon, stabilizers such as crosslinked acrylic polymers of the CARBOPOL 980 type are frequently used. However, these stabilizers have the drawback of reducing the cosmetic performance of shampoos, for example by making the hair more laden and more coarse.

Accordingly, there is a need to develop a detergent cosmetic composition, such as a shampoo, which can overcome such disadvantages found with current cosmetic compositions comprising amino silicones and improve good cosmetic performance on keratin materials, i.e., the hair and the scalp, such as natural hair.

Such detergent compositions, comprising a cationic copolymer as an agent for stabilizing or suspending water-insoluble ingredients such as silicones or fatty substances are described, for example, in International Patent Application No. WO 2005/092 276. However, the foam quality and the cosmetic properties obtained with these compositions are still not sufficiently satisfactory.

The present inventors have discovered that the combination of at least one cationic copolymer and at least one amino silicone makes it possible to overcome these drawbacks.

Specifically, it has been found that the use of the at least one cationic copolymer in the compositions disclosed herein produces on keratin materials, such as the hair, very good cosmetic properties, for instance lightness, softness, smooth feel, suppleness, and manageability of dried hair. It has also been found with the compositions disclosed herein, dried hair may look, for example, smoother.

Moreover, the compositions according to the present disclosure have good rheology, are stable, and have an attractive visual appearance.

Foaming compositions according to the present disclosure, such as shampoos, have foam properties (appearance, consistency, abundance of the foam, elimination of the foam) that are very satisfactory, for instance, rapid initiation of foaming and the foam is eliminated easily.

The compositions disclosed herein, when applied to the skin, such as in the form of a bubble bath or a shower gel, may improve the softness of the skin.

Thus, one aspect of the present disclosure is a novel cosmetic composition comprising, in a cosmetically acceptable medium:

(i)—at least one cationic polymer produced by polymerization of a monomer mixture comprising:
 a) at least one vinyl monomer substituted with at least one amino group,
 b) at least one hydrophobic nonionic vinyl monomer chosen from formulae (I) and (II):

$$CH_2=C(X)Z, \quad\quad (I)$$

$$CH_2=CH-OC(O)R; \quad\quad (II)$$

wherein:
X is chosen from a hydrogen atom and a methyl group;
Z is chosen from the groups $-C(O)OR^1$, $-C(O)NH_2$, $-C(O)NHR^1$, $-C(O)N(R^1)_2$, $-C_6H_5$, $-C_6H_4R^1$, $-C_6H_4OR^1$, $-C_6H_4Cl$, $-CN$, $-NHC(O)CH_3$, $-NHC(O)H$, N-(2-pyrrolidonyl), N-caprolactamyl, $-C(O)NHC(CH_3)_3$, $-C(O)NHCH_2CH_2-NH-CH_2CH_2$-urea, $-Si(R)_3$, $-C(O)O(CH_2)_xSi(R)_3$, $-C(O)NH(CH_2)_xSi(R)_3$, and $-(CH_2)_xSi(R)_3$;
x is an integer ranging from 1 to 6;
each R independently is a $C_1$-$C_{30}$ alkyl group;
each $R^1$ is independently chosen from a $C_1$-$C_{30}$ alkyl group, a $C_2$-$C_{30}$ hydroxyalkyl group, and a $C_1$-$C_{30}$ haloalkyl group;
 c) at least one associative vinyl monomer; and
 e) at least one hydroxylated nonionic vinyl monomer, and
(ii)—at least one amino silicone as defined below.

Another aspect of the present disclosure is a cosmetic composition as defined above and use thereof for giving the hair at least one or more properties chosen from sheen, lightness, softness, a smooth feel and/or suppleness.

Yet another aspect of the present disclosure is a process for treating keratin materials, such as the hair, comprising applying a cosmetic composition as disclosed herein to the keratin materials.

As used herein, "keratin materials" are understood to mean the hair, the eyelashes, the eyebrows, the skin, the nails, mucous membranes, or the scalp, for instance the hair.

Another aspect of the present disclosure is the use of at least one cationic copolymer (i) disclosed herein, or for the manufacture of, a cosmetic composition comprising at least one cationic polymer (iii) other than the at least one cationic polymer (i) and having a cationic charge density of greater than or equal to 4 meq./g and at least one amino silicone.

According to at least one embodiment of the present disclosure is a cationic polymer obtained by polymerization of a monomer mixture comprising a) at least one vinyl monomer substituted with at least one amino group, b) at least one hydrophobic nonionic vinyl monomer, c) at least one associative vinyl monomer, and e) at least one hydroxylated nonionic vinyl monomer. In at east one embodiment, the monomers constituting the cationic copolymer also comprise at least one semi-hydrophobic vinyl surfactant monomer d). The monomers a) to e) are different from each other.

In at least one embodiment, the at least one cationic polymer (i) is a thickening polymer.

As used herein, "thickening polymer" is understood to mean a polymer which, when introduced at 1% by weight into an aqueous or aqueous-alcoholic solution comprising 30% by weight of ethanol, and at pH 7, makes it possible to achieve a viscosity of at least 100 cps at 25° C., and at a shear rate of 1 s$^{-1}$. This viscosity may be measured using a viscometer with cone-plate geometry, for example a Haake RS 600 rheometer. In at least one embodiment, these polymers make it possible to increase the viscosity of the compositions in which they are present by at least 50 cps at 25° C. and at 1 s$^{-1}$.

The at least one cationic polymer (i) used in the composition disclosed herein, and the process for manufacturing them, are described, for example, in International Patent Application Publication No. WO 2004/024 779.

As used herein, "vinyl monomer" is understood to mean a monomer comprising at least one $R_0CH=C(R_0)$— group, wherein each $R_0$ is independently chosen from a hydrogen atom, $C_1$-$C_{30}$ alkyl, —C(O)OH, C(O)OR$_0$', —O—C(O)OR$_0$', —C(O)NHR$_0$', —C(O)NHR$_0$', and C(O)NR$_0$'R$_0$" groups, wherein R$_0$' and R$_0$", which may be identical or different, are chosen from $C_1$-$C_{30}$ alkyl groups. Such vinyl monomers include, for example, (meth)acrylates and (meth)acrylamides are vinyl monomers.

According to the present disclosure, the monomer mixture for preparing the at least one cationic polymer (i) used in the composition disclosed herein comprises at least one vinyl monomer substituted with at least one amino group.

The at least one vinyl monomer substituted with at least one amino group that may be used for the preparation of the at least one cationic polymer (i) disclosed herein, is chosen from basic, polymerizable ethylenically unsaturated monomers. The at least one amine group may be derived from monoamino, diamino, or polyamino alkyl groups, or from heteroaromatic groups comprising a nitrogen atom. The at least one amine group may also be chosen from primary, secondary, and tertiary amines. These monomers may be used in the form of amine or in the form of salt.

According to at least one embodiment, the at least one vinyl monomer substituted with at least one amine group is chosen from:

mono($C_1$-$C_4$)alkylamino($C_1$-$C_8$)alkyl(meth)acrylates,
di($C_1$-$C_4$)alkylamino($C_1$-$C_8$)alkyl(meth)acrylates, such as di($C_1$-$C_4$)alkylamino($C_1$-$C_6$)alkyl (meth)acrylates,
mono($C_1$-$C_4$)alkylamino($C_1$-$C_{10}$)alkyl(meth)acrylamides,
di($C_1$-$C_4$)alkylamino($C_1$-$C_8$)alkyl(meth)acrylamides,
(meth)acrylamides with at least one heterocyclic group comprising a nitrogen atom,
(meth)acrylates with at least one heterocyclic group comprising a nitrogen atom,
nitrogenous heterocycles comprising at least one vinyl group,
and mixtures thereof.

Non-limiting examples of vinyl monomers substituted with at least one amino group that may be mentioned include:

mono- or di($C_1$-$C_4$ alkyl)amino($C_1$-$C_4$ alkyl) (meth)acrylates, such as 2-(N,N-dimethylamino)ethyl (meth)acrylate, 3-(N,N-dimethylamino)propyl(meth)acrylate, 4-(N,N-dimethylamino)butyl (meth)acrylate, (N,N-dimethylamino)-t-butyl(meth)acrylate, 2-(N,N-diethylamino)ethyl (meth)acrylate, 3-(N,N-diethylamino)propyl(meth)acrylate, 4-(N,N-diethylamino)butyl (meth)acrylate, 2-(N,N-dipropylamino)ethyl(meth)acrylate, 3-(N,N-dipropylamino)propyl (meth)acrylate, and 4-(N,N-dipropylamino)butyl(meth)acrylate;

mono- or di($C_1$-$C_4$ alkyl)amino($C_1$-$C_4$ alkyl)(meth)acrylamides, such as N'-(2-N,N-dimethylamino)ethyl(meth)acrylamide and N'-(3-N,N-dimethylamino)propylacrylamide;

(meth)acrylamides or (meth)acrylates with a heterocyclic group comprising a nitrogen atom, such as N-(2-pyridyl)acrylamide, N-(2-imidazolyl)methacrylamide, 2-(4-morpholinyl)ethyl methacrylate, 2-(4-morpholinyl)ethyl acrylate, N-(4-morpholinyl)-methacrylamide, and N-(4-morpholinyl)acrylamide; and nitrogenous heterocycles comprising at least one vinyl group, such as 2-vinylpyridine and 4-vinylpyridine.

When the monomers are in the form of salts, they may be mineral salts, such as hydrochloride, sulfate, and phosphate salts; or organic acid salts, such as acetate, maleate, and fumarate salts.

Among the vinyl monomers substituted with at least one amino group that may be mentioned include, but are not limited to:
3-(N,N-dimethylamino)propyl(meth)acrylate,
N'-(3-N,N-dimethylamino)propyl(meth)acrylamide,
2-(N,N-dimethylamino)ethyl(meth)acrylate,
2-(N,N-diethylamino)ethyl(meth)acrylate,
2-(tert-butylamino)ethyl(meth)acrylate,
2-(N,N-dimethylamino)propyl(meth)acrylamide, and
2-(N,N-dimethylamino)neopentyl acrylate.

The at least one vinyl monomer substituted with at least one amino group may be present in an amount ranging from 10% to 70% by weight, for example, from 20% to 60% by weight, and further such as from 30% to 40% by weight, relative to the total weight of the monomer mixture.

According to the present disclosure, the monomer mixture for preparing the at least one cationic polymer (i), also comprises at least one hydrophobic nonionic vinyl monomer b).

The at least one hydrophobic nonionic vinyl monomer b) for the preparation of the at least one cationic polymer disclosed herein is, in at least one embodiment, chosen from compounds of formulae (I) and (II):

$$CH_2=C(X)Z, \qquad (I)$$

$$CH_2=CH-OC(O)R; \qquad (II)$$

wherein:
X is chosen from a hydrogen atom and a methyl group;
Z is chosen from the groups —C(O)OR$^1$, —C(O)NH$_2$, —C(O)NHR$^1$, —C(O)N(R$^1$)$_2$, —C$_6$H$_5$, —C$_6$H$_4$R$^1$, —C$_6$H$_4$OR$^1$, —C$_6$H$_4$Cl, —CN, —NHC(O)CH$_3$, —NHC(O)H, N-(2-pyrrolidonyl), N-caprolactamyl, —C(O)NHC(CH$_3$)$_3$, —C(O)NHCH$_2$CH$_2$—NH—CH$_2$CH$_2$-urea, —Si(R)$_3$, —C(O)O(CH$_2$)$_x$Si(R)$_3$, —C(O)NH(CH$_2$)$_x$Si(R)$_3$, and —(CH$_2$)$_x$Si(R)$_3$;
x is an integer ranging from 1 to 6;
each R independently is a $C_1$-$C_{30}$ alkyl group;
each R$^1$ independently is a $C_1$-$C_{30}$ alkyl group, a $C_2$-$C_{30}$ hydroxyalkyl group, and a $C_1$-$C_{30}$ haloalkyl group.

Non-limiting mention may be made, for example, of $C_1$-$C_{30}$ alkyl (meth)acrylates; ($C_1$-$C_{30}$ alkyl)(meth)acrylamides; styrene, substituted styrenes, such as vinyltoluene (or 2-methylstyrene), butylstyrene, isopropylstyrene, and para-chlorostyrene; vinyl esters, such as vinyl acetate, vinyl butyrate, vinyl caprylate, vinyl pidolate, and vinyl neodecanoate; unsaturated nitriles, such as (meth)acrylonitrile and acrylonitrile; and unsaturated silanes, such as trimethylvinylsilane, dimethylethylvinylsilane, allyidimethylphenylsilane, allyltrimethylsilane, 3-acrylamidopropyltrimethylsilane, and 3-trimethylsilylpropyl methacrylate.

In at least one embodiment, the at least one hydrophobic nonionic vinyl monomer is chosen from $C_1$-$C_{30}$ alkyl acrylates, $C_1$-$C_{30}$ alkyl methacrylates, and mixtures thereof, such as ethyl acrylate, methyl methacrylate, and 3,3,5-trimethylcyclohexyl methacrylate.

The at least one hydrophobic nonionic vinyl monomer may be present in an amount ranging from 20% to 80% by weight, such as from 20% to 70% by weight, and further such as from 50% to 65% by weight, relative to the total weight of the monomer mixture.

The at least one associative vinyl monomer that may be used for the preparation of the at least one cationic polymer (i) used according to the present disclosure may be chosen, for example, from compounds having an ethylenically unsaturated end (i)' for addition polymerization with other monomers of the system, a polyoxyalkylene central portion (ii)' for giving the polymers selective hydrophilic properties, and a hydrophobic end (iii)' for giving the polymers selective hydrophobic properties.

The ethylenically unsaturated end (i)' of the at least one associative vinyl monomer is derived, for example, from an α,β-ethylenically unsaturated monocarboxylic or dicarboxylic acid or anhydride, such as a $C_3$ or $C_4$ monocarboxylic or dicarboxylic acid or anhydride. Alternatively, the end (i)' of the at least one associative monomer may be derived from an allyl ether or a vinyl ether; from a nonionic urethane monomer substituted with a vinyl group, as described in U.S. Pat. No. 33,156 or in U.S. Pat. No. 5,294,692; or a product of reaction of urea substituted with a vinyl group, described in U.S. Pat. No. 5,011,978.

The central portion (ii)' of the at least one associative vinyl monomer is, for example, a polyoxyalkylene segment comprising 5 to 250 $C_2$-$C_7$ alkylene oxide units, such as 10 to 120 $C_2$-$C_7$ alkylene oxide units, for example, 15 to 60 $C_2$-$C_7$ alkylene oxide units. In at least one embodiment, central portions (ii)' are polyoxyethylene, polyoxypropylene, and polyoxybutylene segments comprising 5 to 150, such as 10 to 100, and further such as 15 to 60 ethylene oxide, propylene oxide, or butylene oxide units, and random or non-random blocks of ethylene oxide, propylene oxide, or butylene oxide units. In another embodiment, the central portions (ii)' are polyoxyethylene segments.

The hydrophobic end (iii)' of the at least one associative monomer is, for example, a hydrocarbon-based fragment belonging to one of the following hydrocarbon classes: a linear alkyl, a $C_2$-$C_{40}$ alkyl substituted with an aryl group (for example a phenyl group), a phenyl substituted with a $C_2$-$C_{40}$ alkyl group, a branched alkyl, an alicyclic group, and a complex ester.

As used herein, "complex ester" means any ester other than a simple ester.

As used herein, "simple ester" means any ester of an unsubstituted, linear or branched saturated $C_1$-$C_{30}$ aliphatic alcohol.

Non-limiting examples of the hydrophobic ends (iii)' of the at least one associative monomer include linear and branched $C_8$-$C_{40}$ alkyl groups, such as capryl($C_8$), isooctyl(branched $C_8$), decyl($C_{10}$), lauryl($C_{12}$), myristyl($C_{14}$), cetyl($C_{16}$), cetearyl($C_{16}$-$C_{18}$), stearyl($C_{18}$), isostearyl(branched $C_{18}$), arachidyl($C_{20}$), behenyl($C_{22}$), lignoceryl($C_{24}$), cerotyl($C_{26}$), montanyl($C_{28}$), melissyl($C_{30}$), and lacceryl($C_{32}$) groups.

Non-limiting examples of linear and branched $C_8$-$C_{40}$ alkyl groups derived from a natural source include alkyl groups derived from hydrogenated groundnut oil, soybean oil and canola oil (predominantly $C_{18}$), $C_{16}$-$C_{18}$ hydrogenated tallow oil; and $C_{10}$-$C_{30}$ hydrogenated terpenols, such as hydrogenated geraniol (branched $C_{10}$), hydrogenated farnesol (branched $C_{15}$), and hydrogenated phytol (branched $C_{20}$).

Non-limiting examples of phenyls substituted with a $C_2$-$C_{40}$ alkyl include octylphenyl, nonylphenyl, decylphenyl, dodecylphenyl, hexadecylphenyl, octadecylphenyl, isooctylphenyl, and sec-butylphenyl.

$C_8$-$C_{40}$ alicyclic groups may be, for example, groups derived from sterols of animal origin, such as cholesterol, lanosterol, and 7-dehydrocholesterol; or derivatives of plant origin, such as phytosterol, stigmasterol, or campesterol; or derivatives obtained from microorganisms, such as ergosterol or mycrosterol. Other useful $C_8$-$C_{40}$ alicyclics that may be used include, but are not limited to, cyclooctyl, cyclododecyl, adamantyl, and decahydronaphthyl, and groups derived from natural $C_8$-$C_{40}$ alicyclics compounds such as pinene, hydrogenated retinol, camphor, and isobornyl alcohol.

The $C_2$-$C_{40}$ alkyl groups substituted with an aryl group may be, for example, 2-phenylethyl, 2,4-diphenylbutyl, 2,4,6-triphenylhexyl, 4-phenylbutyl, 2-methyl-2-phenylethyl, or 2,4,6-tris(1'-phenylethyl)phenyl.

Non-limiting examples of $C_8$-$C_{40}$ complex esters that may be used as end (iii)' include hydrogenated castor oil (for example, 12-hydroxystearic acid triglyceride); 1,2-diacyl glycerols, such as 1,2-distearyl glycerol, 1,2-dipalmitol glycerol, and 1,2-dimyristyl glycerol; di-, tri-, or polyesters of sugars, such as 3,4,6-tristearyl glucose or 2,3-dilauryl fructose; and sorbitan esters such as those described in U.S. Pat. No. 4,600,761.

The at least one associative vinyl monomer that may be used according to the present disclosure may be prepared via any method known in the prior art. Reference may be made, for example, to U.S. Pat. Nos. 4,421,902, 4,384,096, 4,514,552, 4,600,761, 4,616,074, 5,294,692, 5,292,843; 5,770,760, and 5,412,142.

In at least one embodiment, the at least one associative vinyl monomer c) that may be used according to the present disclosure is chosen from compounds of formula (III):

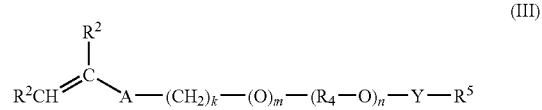

(III)

wherein:
each $R^2$ is independently chosen from a hydrogen atom, a methyl group,
—C(O)OH group, and —C(O)OR$^3$ group;
and $R^3$ is chosen from a $C_1$-$C_{30}$ alkyl;
A is chosen from —CH$_2$C(O)O—, —C(O)O—, —O—, CH$_2$O, —NHC(O)NH—, —C(O)NH—, —Ar—(CE$_2$)$_z$-NHC(O)O—, —Ar—(CE$_2$)$_z$-NHC(O)NH—, and —CH$_2$CH$_2$—NHC(O)—;
Ar is a divalent aryl group (for example a phenyl group);
E is chosen from a hydrogen atom and a methyl group;
z is an integer ranging from 0 to 1;
k is an integer ranging from 0 to 30;
m is an integer ranging from 0 to 1, with the provisos that when k is 0, then m is 0, and when k is an integer ranging from 1 to 30, then m is 1;
($R^4$—O)$_n$ is a polyoxyalkylene, which is a homopolymer, a random copolymer, or a block copolymer, comprising $C_2$-$C_4$ oxyalkylene units;
$R^4$ is chosen from $C_2H_4$, $C_3H_6$, $C_4H_8$, and mixtures thereof;
n is an integer ranging from 5 to 250;

Y is chosen from —R$^4$O—, —R$^4$NH—, —C(O)—, —C(O)NH—, R$^4$NHC(O)NH—, and —C(O)NHC(O)—;

R$^5$ is chosen from substituted and unsubstituted linear C$_8$-C$_{40}$ alkyl groups, branched C$_8$-C$_{40}$ alkyl groups, C$_8$-C$_{40}$ alicyclic groups, phenyls substituted with a C$_2$-C$_{40}$ alkyl group, C$_2$-C$_{40}$ alkyl groups substituted with an aryl group, and C$_8$-C$_{80}$ complex esters, wherein the alkyl group R$^5$ optionally comprises at least one substituent chosen from hydroxyl, alkoxy, and halo groups.

In at least one embodiment, the at least one associative vinyl monomer is chosen from polyethoxylated cetyl(meth)acrylates, polyethoxylated cetearyl (meth)acrylates, polyethoxylated stearyl(meth)acrylates, polyethoxylated arachidyl (meth)acrylates, polyethoxylated behenyl(meth)acrylates, polyethoxylated lauryl (meth)acrylates, polyethoxylated cerotyl(meth)acrylates, polyethoxylated montanyl (meth)acrylates, polyethoxylated melissyl(meth)acrylates, polyethoxylated lacceryl (meth)acrylates, polyethoxylated 2,4,6-tris(1'-phenylethyl)phenyl(meth)acrylates, polyethoxylated hydrogenated castor oil (meth)acrylates, polyethoxylated canola (meth)acrylates, polyethoxylated cholesteryl(meth)acrylates, and mixtures thereof, wherein the polyethoxylated portion of the monomer comprises from 5 to 100 ethylene oxide units, for example, from 10 to 80 ethylene oxide units, and further for example, from 15 to 60 ethylene oxide units.

In another embodiment, the at least one associative vinyl monomer is chosen from polyethoxylated cetyl methacrylates, polyethoxylated cetearyl methacrylates, polyethoxylated stearyl(meth)acrylates, polyethoxylated arachidyl (meth)acrylates, polyethoxylated behenyl(meth)acrylates and polyethoxylated lauryl(meth)acrylates, wherein the polyethoxylated portion of the monomer comprises from 10 to 80 ethylene oxide units, such as from 15 to 60 ethylene oxide units, and further for example from 20 to 40 ethylene oxide units.

In yet another embodiment, the at least one associative vinyl monomer is present in an amount ranging from 0.001% to 25% by weight, for example from 0.01% to 15% by weight, and further for example from 0.1% to 10% by weight, relative to the total weight of the monomer mixture.

The at least one semi-hydrophobic vinyl surfactant monomer optionally present in the monomer mixture can moderate the associative properties of the cationic associative polymers that comprise them, thus may produce aqueous gels having a very good texture and very good rheological properties.

As used herein, "semi-hydrophobic vinyl surfactant monomer" means a monomer with a structure similar to that of an associative monomer, but which has a substantially non-hydrophobic end and thus does not give the polymers associative properties.

The associative property of a polymer is linked to the property in a given medium, of the molecules of the said polymer to associate with each other, or to associate with molecules of a co-agent, such as a surfactant, which is reflected in a certain concentration range by an increase in the viscosity of the medium.

The at least one semi-hydrophobic vinyl surfactant monomer may be compounds comprising two parts:

A. an unsaturated end group to allow addition polymerization with the other monomers of the reaction mixture, and B. a polyoxyalkylene group to attenuate the associations between the hydrophobic groups of the polymer or the hydrophobic groups of the other materials that may be present in the composition comprising the polymer.

The end A providing the vinyl or ethylene unsaturation for the addition polymerization may be, for example, derived from an α,β-ethylenically unsaturated monocarboxylic or dicarboxylic acid or anhydride, such as a C$_3$-C$_4$ monocarboxylic or dicarboxylic acid, or an anhydride of this acid. Alternatively, the end A may be derived from an allylic ether, a vinyl ether, or a nonionic unsaturated urethane.

The polymerizable unsaturated end A may also be derived from a C$_8$-C$_{30}$ unsaturated fatty acid comprising at least one free carboxyl functional group. This C$_8$-C$_{30}$ group forms part of the unsaturated end A and is different from the pendent hydrophobic groups of the associative monomers, which are separated from the unsaturated end of the associative monomer by a hydrophilic spacer group.

The polyoxyalkylene portion B comprises a long-chain polyoxyalkylene segment, which is essentially similar to the hydrophilic portion of the associative monomers. In at least one embodiment, the polyoxyalkylene portions B include C$_2$-C$_4$ polyoxyethylene, polyoxypropylene, and polyoxybutylene units comprising from 5 to 250 oxyalkylene units, such as from 10 to 100 oxyalkylene units. When the at least one semi-hydrophobic vinyl surfactant monomer comprises more than one type of oxyalkylene unit, these units may be distributed randomly, non-randomly, or in blocks.

In at least one embodiment, the at least one semi-hydrophobic vinyl surfactant monomer is chosen from compounds of formula (IV) and (V):

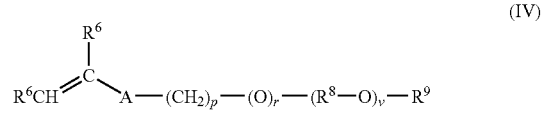

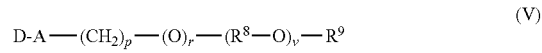

wherein, each R$^6$ independently is chosen from a hydrogen atom, a C$_1$-C$_{30}$ alkyl, —C(O)OH, and C(O)OR$^7$;

wherein R$^7$ is a C$_1$-C$_{30}$ alkyl;

A is chosen from —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$-NHC(O)NH—, and —CH$_2$CH$_2$NHC(O)—;

Ar is a divalent aryl group, for example, a phenyl group;

E is chosen from a hydrogen atom and a methyl group;

z is an integer ranging from 0 to 1;

p is an integer ranging from 0 to 30;

r is an integer ranging from 0 to 1, with the provisos that when p is 0, then r is 0, and when p is an integer ranging from 1 to 30, then r is 1;

(R$_8$—O)$_v$ is a polyoxyalkylene which is a homopolymer, a random copolymer, or a block copolymer comprising C$_2$-C$_4$ oxyalkylene units, wherein R$^8$ is chosen from C$_2$H$_4$, C$_3$H$_6$, C$_4$H$_8$, and mixtures thereof, and v is an integer ranging from 5 to 250;

R$^9$ is chosen from a hydrogen atom and a C$_1$-C$_4$ alkyl group; and

D is chosen from an unsaturated C$_8$-C$_{30}$ alkyl optionally substituted with a carboxyl group.

According to at least one embodiment of the present disclosure, the monomer mixture comprises at least one semi-hydrophobic vinyl surfactant monomer chosen from one of the following formulae:

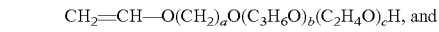

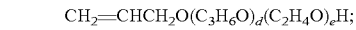

wherein
a is an integer ranging from 2 to 4;
b is an integer ranging from 1 to 10;
c is an integer ranging from 5 to 50;
d is an integer ranging from 1 to 10; and
e is an integer ranging from 5 to 50.

Non-limiting examples of semi-hydrophobic vinyl surfactant monomers include polymerizable emulsifiers sold under the references EMULSOGEN® R109, R208, R307, RAL 109, RAL208, and RAL307 by the company Clariant; BX-AA-E5P5 sold by the company Bimax; and MAX-EMUL® 5010 and 5011 sold by the company UNIQEMA. In at least one embodiment, EMULSOGEN® R208, R307, and RAL 307 may be used.

According to the manufacturers:
EMULSOGEN® R109 is a random ethoxylated/propoxylated 1,4-butanediol vinyl ether having the empirical formula:

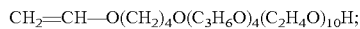
$$CH_2=CH-O(CH_2)_4O(C_3H_6O)_4(C_2H_4O)_{10}H;$$

EMULSOGEN® R208 is a random ethoxylated/propoxylated 1,4-butanediol vinyl ether having the empirical formula:

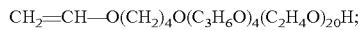
$$CH_2=CH-O(CH_2)_4O(C_3H_6O)_4(C_2H_4O)_{20}H;$$

EMULSOGEN® R307 is a random ethoxylated/propoxylated 1,4-butanediol vinyl ether having the empirical formula:

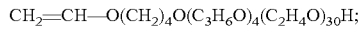
$$CH_2=CH-O(CH_2)_4O(C_3H_6O)_4(C_2H_4O)_{30}H;$$

EMULSOGEN® RAL 109 is a random ethoxylated/propoxylated allylic ether having the empirical formula:

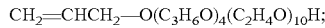
$$CH_2=CHCH_2-O(C_3H_6O)_4(C_2H_4O)_{10}H;$$

EMULSOGEN® RAL 208 is a random ethoxylated/propoxylated allylic ether having the empirical formula:

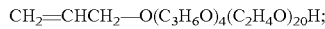
$$CH_2=CHCH_2-O(C_3H_6O)_4(C_2H_4O)_{20}H;$$

EMULSOGEN® RAL 307 is a random ethoxylated/propoxylated allylic ether having the empirical formula:

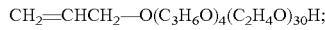
$$CH_2=CHCH_2-O(C_3H_6O)_4(C_2H_4O)_{30}H;$$

MAXEMUL® 5010 is a hydrophobic carboxylated $C_{12}$-$C_{15}$ alkenyl, ethoxylated with 24 ethylene oxide units,
MAXEMUL® 5011 is a hydrophobic carboxylated $C_{12}$-$C_{15}$ alkenyl, ethoxylated with 34 ethylene oxide units; and
BX-AA-E5P5 is a random ethoxylated/propoxylated allylic ether having the empirical formula:

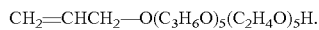
$$CH_2=CHCH_2-O(C_3H_6O)_5(C_2H_4O)_5H.$$

The amount of the at least one semi-hydrophobic vinyl surfactant monomer used in the preparation of the at least one cationic polymer (i) used in the composition according to the present disclosure may vary widely and also depend on the final rheological properties desired for the polymer.

When present, the at least one semi-hydrophobic vinyl surfactant monomer may be present in an amount ranging from 0.01% to 25% by weight, such as from 0.1% to 10% by weight, relative to the total weight of the monomer mixture.

The at least one cationic polymer (i) used in the composition as disclosed herein is prepared from a monomer mixture that may comprise at least one hydroxylated nonionic vinyl monomer, which are ethylenically unsaturated monomers comprising at least one hydroxyl substituent.

Non-limiting examples of hydroxylated nonionic vinyl monomers include hydroxylated $C_1$-$C_6$ alkyl(meth)acrylates, for example hydroxylated $C_1$-$C_4$ alkyl (meth)acrylates, such as 2-hydroxyethyl methacrylate (HEMA), 2-hydroxyethyl acrylate (2-HEA), and 3-hydroxypropyl acrylate; hydroxylated $C_1$-$C_4$ alkyl(meth)acrylamides, such as N-(2-hydroxyethyl)methacrylamide, N-(2-hydroxyethyl)acrylamide, N-(3-hydroxypropyl)-acrylamide, and N-(2,3-dihydroxypropyl)acrylamide; and mixtures thereof. Non-limiting mention may also be made of allyl alcohol, glyceryl monoallyl ether, 3-methyl-3-buten-1-ol, and vinyl alcohol precursors, and equivalents thereof, such as vinyl acetate.

The at least one hydroxylated nonionic vinyl monomer may be present in an amount ranging from 0% to 10% by weight, relative to the total weight of the monomer mixture. In at least one embodiment, the at least one hydroxylated nonionic vinyl monomer is present in an amount ranging from 0.01% to 10% by weight, for example from 1% to 8%, and further for example from 1% to 5% by weight, relative to the total weight of the monomer mixture.

The at least one cationic polymer (i) used in the composition according to the present disclosure is prepared from a monomer mixture that may comprise at least one crosslinking monomer for introducing branches and controlling the molecular mass.

Polyunsaturated crosslinking agents that may be used are well known in the prior art. Monounsaturated compounds with a reactive group capable of crosslinking a copolymer formed before, during or after the polymerization may be used. Other crosslinking monomers that may be used include, but are not limited to, polyfunctional monomers comprising multiple reactive groups such as peroxide, isocyanate groups and hydrolysable silane groups. Many polyunsaturated compounds may be used to generate a partially or substantially crosslinked three-dimensional network.

Non-limiting examples of polyunsaturated crosslinking monomers that may be used include polyunsaturated aromatic monomers, such as divinylbenzene, divinylnaphthalene, and trivinylbenzene; polyunsaturated alicyclic monomers such as 1,2,4-trivinylcyclohexane; difunctional phthalic acid esters such as diallyl phthalate; polyunsaturated aliphatic monomers such as dienes, trienes, and tetraenes, such as isoprene, butadiene, 1,5-hexadiene, 1,5,9-decatriene, 1,9-decadiene, and 1,5 heptadiene.

Other non-limiting examples of polyunsaturated crosslinking monomers that may be used include polyalkenyl ethers, such as triallylpentaerythritol, diallylpentaerythritol, diallylsucrose, octaallylsucrose, and trimethylolpropane diallyl ether; polyunsaturated esters of polyalcohols or of polyacids, such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, and polyethylene glycol di(meth)acrylate; alkylenebisacrylamides, such as methylenebisacrylamide and propylenebisacrylamide; hydroxylated and carboxylated derivatives of methylenebisacrylamide, such as N,N'-bismethylol methylenebisacrylamide; polyethylene glycol di(meth)acrylates, such as ethylene glycol di(meth)acrylate, diethylene glycol di(meth)acrylate, and triethylene glycol di(meth)acrylate; polyunsaturated silanes, such as dimethyldivinylsilane, methyltrivinylsilane, allyldimethylvinylsilane, diallyidimethylsilane, and tetravinylsilane; and polyunsaturated stannanes, such as tetraallyltin and diallyldimethyltin.

Non-limiting examples of monounsaturated crosslinking monomers that may be used and that bear a reactive group may be N-methylolacrylamides; N-alkoxy(meth)acrylamides, wherein the alkoxy group is a $C_1$-$C_{18}$ group; and unsaturated hydrolysable silanes, such as triethoxyvinylsilane, tris-isopropoxyvinylsilane, and 3-triethoxysilylpropyl methacrylate.

Polyfunctional crosslinking monomers that comprise several reactive groups and that may be mentioned, by way of non-limiting example, include hydrolysable silanes such as ethyltriethoxysilane and ethyltrimethoxysilane; epoxidized hydrolysable silanes such as 2-(3,4-epoxycyclohexyl)ethyltriethoxysilane and 3-glycidoxy-propyltrimethyoxysilane; polyisocyanates, such as 1,4-diisocyanatobutane, 1,6-diisocyanatohexane, 1,4-phenylenediisocyanate, and 4,4'-oxybis (phenylisocyanate); unsaturated epoxides, such as glycidyl methacrylate and allyl glycidyl ether; and polyepoxides, such as diglycidyl ether, 1,2,5,6-diepoxyhexane, and ethylene glycol diglycidyl ether.

Further non-limiting examples of polyunsaturated crosslinking monomers include ethoxylated polyols, such as diols, triols, and bis-phenols, ethoxylated with from 2 to 100 mol of ethylene oxide per mole of hydroxyl functional group and ending with a polymerizable unsaturated group such as a vinyl ether, an allyl ether, an acrylate ester, or a methacrylate ester. Such crosslinking monomers may be, for example, ethoxylated bisphenol A dimethacrylate, ethoxylated bisphenol F dimethacrylate, and ethoxylated trimethylolpropane trimethacrylate.

Other non-limiting examples of ethoxylated crosslinking monomers that may be used herein include the crosslinking agents derived from ethoxylated polyols described in U.S. Pat. No. 6,140,435.

According to at least one embodiment of the present disclosure, the crosslinking monomers are acrylate and methacrylate esters of polyols comprising at least two acrylate or methacrylate ester groups, such as trimethylolpropane triacrylate (TMPTA), trimethylolpropane dimethacrylate, triethylene glycol dimethacrylate (TEGDMA), and ethoxylated (30) bisphenol A dimethacrylate (EOBDMA).

The at least one crosslinking monomer may be present in an amount ranging from 0% to 5% by weight, relative to the weight of the monomer mixture. In at least one embodiment, the at least one crosslinking monomer is present in an amount ranging from 0.001% to 5% by weight, for example, from 0.05% to 2% by weight, and further, for example, from 0.1% to 1% by weight, relative to the total weight of the monomer mixture.

The monomer mixture may further comprise at least one chain-transfer agent.

Non-limiting mention may be made of chain-transfer agents, for example, thiol compounds, disulfide compounds, such as $C_1$-$C_{18}$ mercaptans, mercaptocarboxylic acids, mercaptocarboxylic acid esters, thioesters, $C_1$-$C_{18}$ alkyl disulfides, aryl disulfides, and polyfunctional thiols; phosphites and hypophosphites; haloalkyl compounds such as carbon tetrachloride and bromotrichloromethane; and unsaturated chain-transfer agents, such as α-methylstyrene.

The polyfunctional thiols are, for example, trifunctional thiols, such as trimethylolpropane tris(3-mercaptopropionate), tetrafunctional thiols, such as pentaerythritol tetrakis (thioglycolate) and pentaerythritol tetrakis(thiolactate); hexafunctional thiols, such as pentaerythritol hexakis (thioglycolate).

In another embodiment, the at least one chain-transfer agent may be at least one catalytic chain-transfer agent that reduces the molecular weight of the addition polymers during the free-radical polymerization of the vinyl monomers. Examples that may be mentioned include, but are not limited to cobalt complexes, such as cobalt (II) chelates. The at least one catalytic chain-transfer agent may also be used at low concentrations relative to the thiolated chain-transfer agents.

Non-limiting examples of the at least one chain-transfer agent that may be mentioned include octyl mercaptan, n-dodecyl mercaptan, t-dodecyl mercaptan, hexadecyl mercaptan, octadecyl mercaptan (ODM), isooctyl 3-mercapto-propionate (IMP), butyl 3-mercaptopropionate, 3-mercaptopropionic acid, butyl thioglycolate, isooctyl thioglycolate, and dodecyl thioglycolate.

The at least one chain-transfer agent may be present in an amount ranging from 0% to 10% by weight, relative to the total weight of the monomer mixture. In at least one embodiment, the at least one chain-transfer agent is present in an amount ranging from 0.1% to 5% by weight, relative to the total weight of monomers.

The monomer mixture for preparing the at least one cationic polymer (i) used in the composition according to the present disclosure may comprise at least one polymeric stabilizer for obtaining stable dispersions or emulsions. In at least one embodiment, the at least one polymer is water-soluble. Non-limiting examples of synthetic polymers include polyvinyl alcohols, partially hydrolysed polyvinyl acetates, polyvinylpyrrolidone, polyacrylamides, polymethacrylamides, carboxylated addition polymers, and polyalkyl vinyl ethers; water-soluble natural polymers, such as gelatin, pectins, alginates, and casein; and modified natural polymers, such as methylcellulose, hydroxypropylcellulose, carboxymethylcellulose, and allylic hydroxyethylcelluloses.

The at least one polymeric stabilizer may be present in an amount ranging from 0% to 2% by weight, relative to the total weight of the monomer mixture, for example, ranging from 0.0001% and 1% by weight, and further, for example, ranging from 0.01% and 0.5% by weight, relative to the weight of the monomer mixture.

According to one embodiment, the monomer mixture comprises, relative to the total weight of the monomer mixture:
a) from 10% to 70% by weight of at least one vinyl monomer substituted with at least one amino group,
b) from 20% to 80% by weight of at least one hydrophobic nonionic vinyl monomer,
c) from 0.001% to 25% by weight of at least one associative vinyl monomer,
d) from 0 to 25% by weight of at least one semi-hydrophobic vinyl surfactant monomer,
e) from 0 to 10% by weight of at least one hydroxylated nonionic vinyl monomer,
f) from 0 to 5% by weight of at least one crosslinking monomer,
g) from 0 to 10% by weight of at least one chain-transfer agent, and
h) from 0 to 2% by weight of at least one polymeric stabilizer.

In at least one embodiment, the monomer mixture comprises, relative to the total weight of the monomer mixture:
a) from 20% to 60% by weight of at least one vinyl monomer substituted with at least one amino group,
b) from 20% to 70% by weight of at least one hydrophobic nonionic vinyl monomer,
c) from 0.01% to 15% by weight of at least one associative vinyl monomer,
d) from 0.1% to 10% by weight of at least one semi-hydrophobic vinyl surfactant monomer,
e) from 0.01% to 10% by weight of at least one hydroxylated nonionic vinyl monomer,
f) from 0.001% to 5% by weight of at least one crosslinking monomer,
g) from 0.001% to 10% by weight of at least one chain-transfer agent, and
h) from 0 to 2% by weight of at least one polymeric stabilizer.

According to at least one embodiment of the present disclosure, the monomer mixture for preparing the at least one cationic polymer (i) used in the composition disclosed herein comprises, relative to the total weight of the monomer mixture:

a) from 20% to 50% by weight of at least one vinyl monomer substituted with at least one amino group chosen from:
3-(N,N-dimethylamino)propyl(meth)acrylate,
N'-(3-N,N-dimethylamino)propyl(meth)acrylamide,
2-(N,N-dimethylamino)ethyl(meth)acrylate,
2-(N,N-diethylamino)ethyl(meth)acrylate,
2-(tert-butylamino)ethyl(meth)acrylate,
2-(N,N-dimethylamino)propyl(meth)acrylamide, and
2-(N,N-dimethylamino)neopentyl acrylate, b) from 50% to 65% by weight of at least one hydrophobic nonionic vinyl monomer chosen from $C_1$-$C_{30}$ alkyl esters of acrylic acid, $C_1$-$C_{30}$ alkyl esters of methacrylic acid, and mixtures thereof, c) from 0.1% to 10% by weight of at least one associative vinyl monomer chosen from polyethoxylated cetyl methacrylates, polyethoxylated cetearyl methacrylates, polyethoxylated stearyl(meth)acrylates, polyethoxylated arachidyl (meth)acrylates, polyethoxylated behenyl(meth)acrylates, polyethoxylated lauryl(meth)acrylates, polyethoxylated cerotyl(meth)acrylates, polyethoxylated montanyl(meth) acrylates, polyethoxylated melissyl (meth)acrylates, polyethoxylated lacceryl(meth)acrylates, polyethoxylated 2,4,6-tris(1'-phenylethyl)phenyl (meth)acrylates, polyethoxylated hydrogenated castor oil (meth)-acrylates, polyethoxylated canola (meth)acrylates, polyethoxylated cholesteryl (meth) acrylates, and mixtures thereof, d) from 0.1% to 10% by weight of at least one semi-hydrophobic vinyl surfactant monomer chosen from one of the following formulae:

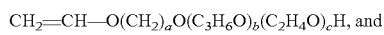

$CH_2=CH-O(CH_2)_aO(C_3H_6O)_b(C_2H_4O)_cH$, and

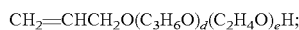

$CH_2=CHCH_2O(C_3H_6O)_d(C_2H_4O)_eH$;

wherein:
a is an integer ranging from 2 to 4;
b is an integer ranging from 1 to 10;
c is an integer ranging from 5 to 50;
d is an integer ranging from 1 to 10; and
e is an integer ranging from 5 to 50;

e) from 0% to 10% by weight of at least one hydroxylated nonionic vinyl monomer, f) from 0% to 5% by weight of at least one crosslinking monomer, g) from 0% to 10% by weight of at least one chain-transfer agent, and h) from 0% to 2% by weight of at least one polymeric stabilizer.

In at least one embodiment, the at least one cationic polymer (i) disclosed herein is chosen from polymers derived from the polymerization of the following monomer mixture:
a di($C_1$-$C_4$ alkyl)amino($C_1$-$C_6$ alkyl)methacrylate,
at least one $C_1$-$C_{30}$ alkyl ester of (meth)acrylic acid,
a $C_{10}$-$C_{30}$ alkyl methacrylate polyethoxylated comprising from 20 to 30 mol of ethylene oxide,
a 30/5 polyethylene glycol/polypropylene glycol allyl ether,
a hydroxy($C_2$-$C_6$ alkyl)methacrylate, and
an ethylene glycol dimethacrylate.

Among the cationic polymers (i) disclosed herein, mention may be made, in a non-limiting manner, of the compound sold by the company Noveon under the name CARBOPOL Aqua CC Polymer and which corresponds to the INCI name Polyacrylate-1 Crosspolymer.

Polyacrylate-1 Crosspolymer is the product of polymerization of a monomer mixture comprising:
a di($C_1$-$C_4$ alkyl)amino($C_1$-$C_6$ alkyl)methacrylate,
at least one $C_1$-$C_{30}$ alkyl ester of (meth)acrylic acid,
a polyethoxylated $C_{10}$-$C_{30}$ alkyl methacrylate (20-25 mol of ethylene oxide units),
a 30/5 polyethylene glycol/polypropylene glycol allyl ether,
a hydroxy($C_2$-$C_6$ alkyl)methacrylate, and
an ethylene glycol dimethacrylate.

The at least one cationic polymer (i) used in the compositions according to the present disclosure may be present in an amount ranging from 0.01% to 10% by weight, for example from 0.05% to 5% by weight, and further for example from 0.1% to 1% by weight, relative to the total weight of the composition.

The at least one cationic polymer (i) used in the composition according to the present disclosure may be prepared via conventional polymerization techniques, such as emulsion polymerization. The polymerization may be performed via a simple batch process, or via a controlled addition process, or the reaction may be initiated in a small reactor and the mass of monomers may then be added in a controlled manner to the reactor (seeding process). For example, the polymerization may be performed at a reaction temperature ranging from 20 to 80° C., although higher or lower temperatures may be used. To facilitate the emulsification of the monomer mixture, the emulsion polymerization is performed in the presence of a surfactant that is present in an amount ranging from 1% to 10% by weight, such as from 3% to 8% by weight, and further, for example, from 5% to 7% by weight, relative to the total weight of the emulsion. The emulsion polymerization reaction medium also comprises at least one radical initiator, which may be present, for example, in an amount ranging from 0.01% to 3% by weight, relative to the total weight of the monomer mixture. The polymerization may be performed in an aqueous or aqueous-alcoholic medium at a neutral or weakly alkaline pH.

In a typical polymerization, the monomer mixture is added with stirring to a solution of emulsifying surfactants, such as a nonionic surfactant, for instance, a linear or branched alcohol ethoxylate, or a mixture of nonionic and anionic surfactants, such as fatty alkyl sulfates or alkyl sulfonates of fatty alcohols, in a suitable amount of water, in a suitable reactor, to prepare the monomer emulsion. The emulsion is deoxygenated via any known method, and the polymerization reaction is then initiated by adding a polymerization catalyst (initiator) such as sodium persulfate, or any other suitable addition polymerization catalyst, as is well known in the field of polymers. The reaction is stirred until the polymerization is complete, for example, for a time ranging from 4 hours to 16 hours. The monomer emulsion may be heated to a temperature ranging from 20 to 80° C. before adding the initiator, if so desired. The amount of unreacted monomers may be removed by adding an additional amount of catalyst. The polymer emulsion obtained may be discharged from the reactor and packaged for storage or used. Optionally, the pH or other physical or chemical characteristics of the emulsion may be adjusted before discharging the emulsion from the reactor. The emulsion produced can have a total solids content ranging between 10% and 40% by weight. The total amount of polymers in the emulsion obtained can range between 15% and 35% by weight, and, for example, can be at most 25% by weight.

Surfactants that are suitable for facilitating the emulsion polymerization include, but are not limited to, surfactants conventionally used in emulsion polymerizations, such as nonionic, anionic, amphoteric, and cationic surfactants, and mixtures thereof. In at least one embodiment, nonionic, anionic surfactants, and mixtures thereof are used.

The polymerization may be performed in the presence of at least one free-radical initiator. These initiators may be chosen from insoluble inorganic persulfate compounds, such as ammonium persulfate, potassium persulfate, and sodium persulfate; peroxides, such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid; and oil-soluble free-radical generators, such as 2,2'-azobisisobutyronitrile, and mixtures thereof. The peroxides and peracids may be optionally activated with reducing agents, such as sodium bisulfite or ascorbic acid, transition metals or hydrazine. Suitable free-radical initiators include, but are not limited to, water-soluble azo polymerization initiators such as 2,2'-azobis(tert-alkyl) compounds bearing a water-solubilizing substituent on the alkyl group. Non-limiting examples of azo polymerization catalysts that may be used include the VAZO® free-radical initiators sold by the company DuPont, VAZO® 44 (2,2'-azobis(2-4,5-dihydroimidazolyl)propane), VAZO®56 (2,2'-azobis(2-methylpropionamidine) dihydrochloride), and VAZO® 68 (4,4'-azobis(4-cyanovaleric acid)).

As used herein, "amino silicone" means any silicone comprising at least one primary, secondary, or tertiary amine function or at least one quaternary ammonium group.

The at least one amino silicone used in the cosmetic composition according to the present disclosure is chosen from:

a) amino silicones comprising at least one primary amine function of formula (VI):

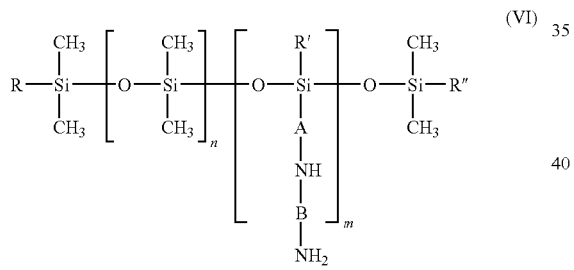

wherein R, R', and R", which may be identical or different, are chosen from $C_1$-$C_4$ alkyl radicals, such as $CH_3$, $C_1$-$C_4$ alkoxy radicals, for instance methoxy groups; and OH; A and B are independently chosen from linear and branched, $C_2$-$C_8$ alkylene radicals, for example, A is chosen from $C_3$-$C_6$ alkylene radicals and B is chosen from $C_2$-$C_4$ alkylene radicals, with the proviso that R and R" are not simultaneously hydroxyl groups, and m and n are integers that depend on the molecular weight and whose sum ranges from 1 to 2000, and b) amino silicones comprising at least non-amidated quaternized amine function.

As used herein, "non-amidated silicone" is understood to mean a silicone that does not comprise any amide functions (—NHC(O)—).

According to one embodiment of the present disclosure, R, R', and R", which may be identical or different, are chosen from $C_1$-$C_4$ alkoxy and hydroxyl radicals, wherein at least one of the radicals R or R" is an alkoxy radical and A is a $C_3$ alkylene radical. The hydroxyl/alkoxy molar ratio is, for example, between 0.2/1 and 0.4/1 and advantageously equal to 0.3/1. Moreover, m and n are such that the weight-average molecular mass of the compound may range between 2000 and $10^6$, for example, n is an integer between 0 and 999 and m is an integer between 1 and 1000, the sum of n and m being between 1 and 1000.

In this category of compounds, mention may be made, by way of non-limiting example, of the product BELSILI® ADM 652 sold by Wacker.

According to another embodiment, R and R", which are different, are chosen from a $C_1$-$C_4$ alkoxy radical and hydroxyl radical, wherein at least one of the radicals R or R" is an alkoxy radical, R' is a methyl radical, and A is a $C_3$ alkylene radical. The hydroxyl/alkoxy molar ratio is, for instance, between 1/0.8 and 1/1.1, and is in at least one embodiment, equal to 1/0.95. Moreover, m and n are such that the weight-average molecular mass of the compound may be between 2000 and 200 000, for instance, n is an integer between 0 and 999 and m is an integer between 1 and 1000, the sum of n and m being between 1 and 1000.

In at least one embodiment, non-limiting mention may be made of the product FLUID WR® 1300 sold by the company Wacker.

Another non-limiting example of an amino silicone is the polymer known in the CTFA dictionary as "trimethylsilyl amodimethicone," of formula (VII):

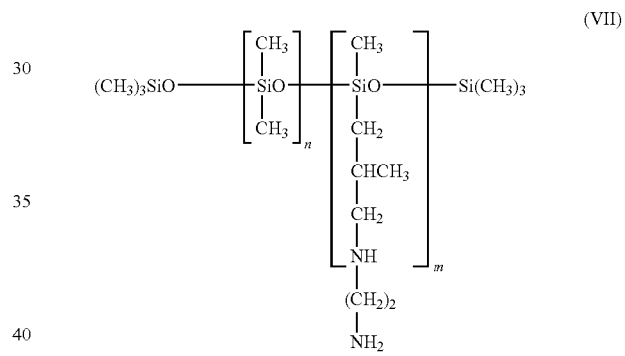

wherein n and m have the meanings given above in accordance with formula (VI).

Such compounds are described, for example, in European Patent Application No. EP 0 095 238; a compound of formula (VII) is sold, for example, under the name Q2-8220 by the company OSI.

The amino silicones comprising at least one non-amidated quaternized amine function are chosen, for example, from:

1) the quaternary ammonium silicones of formula:

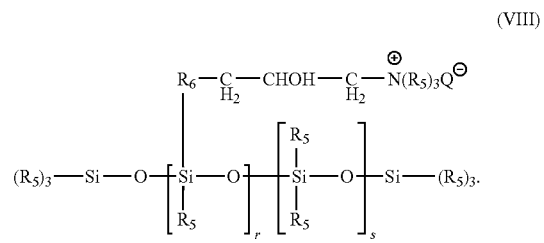

wherein:

$R_5$ is chosen from a monovalent $C_1$-$C_{18}$ hydrocarbon-based radical, such as a $C_1$-$C_{18}$ alkyl radical or a $C_2$-$C_{18}$ alkenyl radical, for example methyl;

$R_6$ is chosen from a divalent hydrocarbon-based radical, such as a $C_1$-$C_{18}$ alkylene radical or a divalent $C_1$-$C_{18}$, for example $C_1$-$C_8$ alkyleneoxy radical connected to Si via a SiC bond;

$Q^-$ is an anion such as a halide ion, for example chloride or an organic acid salt (acetate etc.);

r is an average statistical value ranging from 2 to 20 and, in at least one embodiment, from 2 to 8;

s is an average statistical value ranging from 20 to 200 and, in at least one embodiment, from 20 to 50.

Such amino silicones are described, for example, in U.S. Pat. No. 4,185,087.

(2) the quaternary ammonium silicones of formula:

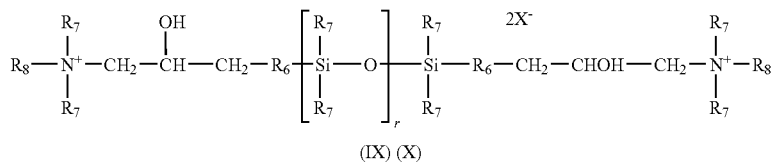

(IX) (X)

wherein:

$R_7$, which may be identical or different, is chosen from a monovalent $C_1$-$C_{18}$ hydrocarbon-based radical, such as a $C_1$-$C_{18}$ alkyl radical, a $C_2$-$C_{18}$ alkenyl radical, and a ring comprising 5 or 6 carbon atoms, for example a methyl group;

$R_6$ is chosen from a divalent hydrocarbon-based radical, such as a $C_1$-$C_{18}$ alkylene radical and a divalent $C_1$-$C_{18}$ radical, for example a $C_1$-$C_8$ alkyleneoxy radical linked to the Si via a SIC bond;

$R_8$, which may be identical or different, is chosen from a hydrogen atom and a monovalent $C_1$-$C_{18}$ hydrocarbon-based radical, such as a $C_1$-$C_{18}$ alkyl radical and a $C_2$-$C_{18}$ alkenyl radical;

$X^-$ is an anion such as a halide ion, for example chloride, or an organic acid salt (for example, acetate);

r is a mean statistical value ranging from 2 to 200 and, in at least one embodiment, from 5 to 100.

These silicones are described, for example, in European Patent Application No. EP-A 0 530 974.

It should be noted that the molecular mass of these silicones is determined by gel permeation chromatography (room temperature, polystyrene standard, μ styragem columns; THF eluent; flow rate of 1 mm/minute; 200 μl of a solution at 0.5% by weight of silicone in THF are injected and detection is performed by refractometry and UV-metry).

According to at least one embodiment of the present disclosure, these compositions further comprise cationic and/or nonionic surfactants.

Another commercial product that may be used according to the present disclosure is the product sold, for example, under the name DOW CORNING Q2 7224 by the company Dow Corning, comprising in combination the trimethylsilyl amodimethicone of formula (VII) described above, a non-ionic surfactant of formula: $C_8H_{17}$—$C_6H_4$—$(OCH_2CH_2)_{40}$—OH, which is known under the CTFA name Octoxynol-40, a second nonionic surfactant of formula: $C_{12}H_{25}$—$(OCH_2$—$CH_2)_6$—OH, which is known under the CTFA name Isolaureth-6, and propylene glycol.

As disclosed herein, all these silicones may also be used in the form of emulsions or microemulsions.

According to the present disclosure, the amino silicones defined above may be present in an amount ranging from 0.001% to 20% by weight, for example, from 0.01% to 10% by weight, and, further for example, from 0.1% to 3% by weight, relative to the total weight of the final composition.

According to at least one embodiment of the present disclosure, the compositions disclosed herein further comprise at least one silicone not already described, or another agent that is beneficial to keratin material, such as the hair, for example, esters of $C_1$-$C_{30}$ carboxylic acids, $C_1$-$C_{30}$ mono- or polyhydroxylated alcohols, plant, animal, mineral or synthetic oils, waxes, ceramides, pseudoceramides, and cationic polymers.

The additional silicones that may be used in accordance with the present disclosure are, for instance, polyorganosiloxanes that are insoluble in the composition and may be in the form of oils, waxes, resins or gums.

These additional organopolysiloxanes are defined, for example, in Walter Noll's "Chemistry and Technology of Silicones" (1968) Academic Press. They may be volatile or non-volatile.

When they are volatile, the additional silicones are, for instance, chosen from those having a boiling point of between 60° C. and 260° C., such as:

(i) cyclic silicones comprising from 3 to 7 silicon atoms, for example, 4 to 5 silicon atoms. These are, for example, octamethylcyclotetrasiloxane sold under the name VOLATILE SILICONE 7207 by Union Carbide or SILBIONE 70045 V 2 by Rhodia Chimie, decamethylcyclopentasiloxane sold under the name VOLATILE SILICONE 7158 by Union Carbide, SILBIONE 70045 V 5 by Rhodia Chimie, and mixtures thereof.

Non-limiting mention may also be made of cyclocopolymers of the dimethylsiloxanes/methylalkylsiloxane type, such as VOLATILE SILICONE FZ 3109 sold by the company Union Carbide, with the chemical structure:

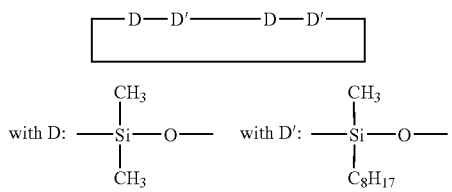

Mention may also be made, by way of non-limiting example, of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2',2',3,3'-hexatrimethylsilyloxy)neopentane;

(ii) linear volatile silicones comprising 2 to 9 silicon atoms and having a viscosity of less than or equal to $5\times10^{-6}$ m$^2$/s at 25° C., for example, decamethyltetrasiloxane sold under the name SH 200 by the company Toray Silicone. Silicones belonging to this category are also described, for instance, in the article published in Cosmetics and Toiletries, Vol. 91, Jan. 76, pp. 27-32, Todd & Byers "Volatile Silicone Fluids for Cosmetics".

These additional silicones may be chosen, for example, from polyalkylsiloxanes, among which mention may be made of polydimethylsiloxanes comprising trimethylsilyl end groups having a viscosity of from $5\times10^{-6}$ to 2.5 m$^2$/s at 25° C., such as $1\times10^{-5}$ to 1 m$^2$/s. The viscosity of the silicones is measured, for example, at 25° C. according to ASTM standard 445 Appendix C.

Among these polyalkylsiloxanes, mention may be made, in a non-limiting manner, of the following commercial products:

the SILBIONE oils of the 47 and 70 047 series or the MIRASIL oils sold by Rhodia Chimie, such as, the oil 70 047 V500 000;

the oils of the MIRASIL series sold by the company Rhodia Chimie;

the oils of the 200 series from the company Dow Corning, for example, DC200 with a viscosity of 60 000 cSt; and the VISCASIL oils from General Electric and certain oils of the SF series (SF 96, SF 18) from General Electric.

Mention may also be made, by way of non-limiting example, of polydimethylsiloxanes comprising dimethylsilanol end groups (Dimethiconol according to the CTFA name) such as the oils of the 48 series from the company Rhodia Chimie.

Non-limiting examples of polyalkylsiloxanes include poly($C_1$-$C_{20}$)alkylsiloxanes, for example, the products sold under the names ABIL WAX 9800 and 9801 by the company Goldschmidt.

The silicone gums which can be used as additive are, for instance, polydiorganosiloxanes having high number-average molecular masses of between 200,000 and 1,000,000, used alone or as a mixture in a solvent. This solvent can be chosen, for example, from volatile silicones, polydimethylsiloxane (PDMS) oils, polyphenylmethyl-siloxane (PPMS) oils, isoparaffins, polyisobutylenes, methylene chloride, pentane, dodecane, tridecanes, and mixtures thereof.

Non-limiting mention may be made, for instance, of the following products:

polydimethylsiloxane, and
polydimethylsiloxane/methylvinylsiloxane gums.

Products that may be used according to the present disclosure, include, but are not limited to mixtures such as:

mixtures formed from a polydimethylsiloxane hydroxylated at the end of the chain (known as dimethiconol according to the nomenclature of the CTFA dictionary) and of a cyclic polydimethylsiloxane (known as cyclomethicone according to the nomenclature of the CTFA dictionary), such as the product Q2 1401 sold by the company Dow Corning;

mixtures formed from a polydimethylsiloxane gum with a cyclic silicone, such as the product SF 1214 SILICONE FLUID from the company General Electric, this product being an SF 30 gum corresponding to a dimethicone, having a number-average molar weight of 500 000, dissolved in the oil SF 1202 SILICONE FLUID corresponding to decamethylcyclopentasiloxane; and mixtures of two PDMSs of different viscosities, such as a PDMS gum and a PDMS oil, for example, the product SF 1236 from the company General Electric. The product SF 1236 is a mixture of an SE 30 gum defined above, with a viscosity of 20 m$^2$/s, and of an SF 96 oil with a viscosity of $5\times10^{-6}$ m$^2$/s and comprises, for instance, 15% SE 30 gum and 85% of an SF 96 oil.

The organopolysiloxane resins that may be used as additive are crosslinked siloxane systems comprising the following units:

$R_2SiO_{2/2}$, $R_3SiO_{1/2}$, $RSiO_{3/2}$, and $SiO_{4/2}$ wherein R is chosen from $C_1$-$C_{16}$ hydrocarbon groups and a phenyl group.

Among these products, non-limiting mention may be made of a product wherein R is chosen from $C_1$-$C_4$ lower alkyl radicals, for example, methyl or a phenyl radical.

Among these resins, mention may be made, by way of non-limiting example, of the product sold under the name DOW CORNING 593 or those sold under the names SILICONE FLUID SS 4230 and SS 4267 by the company General Electric, which are silicones of dimethyl/trimethyl siloxane structure.

Mention may also be made, for instance, of the trimethyl siloxysilicate type resins sold, for example, under the names X22-4914, X21-5034, and X21-5037 by the company Shin-Etsu.

According to the present disclosure, all the silicones may be used in unmodified form or in the form of solutions, emulsions, nanoemulsions, or microemulsions.

In at least one embodiment, the silicones are chosen from:

non-volatile silicones from the family of polyalkylsiloxanes comprising trimethylsilyl end groups, such as oils with a viscosity between 0.2 and 2.5 m$^2$/s at 25° C., such as the oils of the DC200 series from Dow Corning, for example, the product of viscosity 60 000 cSt, of the SILBIONE 70047 and 47 series, such as the oil 70 047 V 500 000, sold by the company Rhodia Chimie, and polyalkylsiloxanes comprising dimethylsilanol end groups, such as dimethiconols or polyalkylarylsiloxanes, such as the oil SILBIONE 70641 V 200 sold by the company Rhodia Chimie; and the organopolysiloxane resin sold under the name DOW CORNING 593.

According to the present disclosure, the additional silicones or the other additional beneficial agents can be present in an amount ranging from 0.001% to 20% by weight, for example, from 0.01% to 10% by weight, and further, for example, from 0.1% to 5% by weight, relative to the total weight of the final composition.

The compositions disclosed herein may further comprise at least one surfactant, which is present in an amount ranging from approximately 0.01% to 50% by weight, such as from approximately 0.1% to 40%, and further, for example, from approximately 0.5% to 30% by weight, relative to the total weight of the composition.

The at least one surfactant may be chosen, for instance, from anionic, amphoteric, nonionic, cationic surfactants, and mixtures thereof.

Suitable surfactants include, but are not limited to:

(i) Anionic Surfactants:

Non-limiting examples of anionic surfactants include salts, for example, alkaline salts, such as sodium salts, ammonium salts, amine salts, amino alcohol salts, and magnesium salts of the following compounds: alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, wherein the alkyl or acyl radical of all of these various compounds comprise, for example, from 8 to 24 carbon atoms, and the aryl radical, in at least one embodiment, is a phenyl or benzyl group. Other useful anionic surfactants include, but are not limited to fatty acid salts such as the salts of oleic, ricinoleic, palmitic and stearic acids, coconut oil acid, or hydrogenated coconut oil acid; acyl lactylates wherein the acyl radical comprises 8 to 20 carbon atoms. Mention may also be made of weakly anionic surfactants, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, such as those comprising from 2 to 50 ethylene oxide groups, and mixtures thereof.

In at least one embodiment, alkyl sulfate salts, alkyl ether sulfate salts, and mixtures thereof are used as anionic surfactants.

(ii) Nonionic Surfactants:

The nonionic surfactants are compounds that are well known (see, for example, "Handbook of Surfactants" by M. R. Porter, published by Blackie & Son (Glasgow and London), 1991, pp. 116-178) and, in the context of the present disclosure, their nature is not a critical feature. Thus, they can be chosen, for instance, from polyethoxylated, polypropoxylated, and polyglycerolated fatty acids, alkylphenols, α-diols, and alcohols having a fatty chain comprising, for example, 8 to 18 carbon atoms, it being possible for the number of ethylene oxide or propylene oxide groups to range, for example, from 2 to 50 and for the number of glycerol groups to range, for instance, from 2 to 30. Non-limiting mention may also be made of copolymers of ethylene oxide and of propylene oxide, condensates of ethylene oxide and of propylene oxide with fatty alcohols; polyethoxylated fatty amides having, for instance, from 2 to 30 mol of ethylene oxide, polyglycerolated fatty amides comprising on average 1 to 5, such as 1.5 to 4, glycerol groups; polyethoxylated fatty amines having, for example, 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides, and N-acylaminopropylmorpholine oxides. In at least one embodiment, alkylpolyglycosides are used.

(iii) Amphoteric Surfactants:

Suitable examples of amphoteric surfactants include, but are not limited to aliphatic secondary and tertiary amine derivatives wherein the aliphatic radical is a $C_8$-$C_{22}$ linear or branched chain comprising at least one water-soluble anionic group, for example carboxylate, sulfonate, sulfate, phosphate, and phosphonate; non-limiting mention may also be made of ($C_8$-$C_{20}$)alkylbetaines, sulfobetaines, ($C_8$-$C_{20}$)alkylamido-($C_1$-$C_6$)alkylbetaines, and ($C_8$-$C_{20}$)alkylamido($C_1$-$C_6$)alkylsulfobetaines.

Among the ($C_8$-$C_{20}$)alkylamido($C_1$-$C_6$)alkylbetaines that may be mentioned include, but are not limited to, the cocoamidopropylbetaine sold, for example, by Goldschmidt under the name TEGOBETAINE F50.

Among the amine derivatives, non-limiting mention may be made, for example, of the products sold under the name MIRANOL, as described in U.S. Pat. Nos. 2,528,378 and 2,781,354 and having the structures:

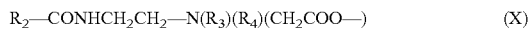

$R_2$—CONHCH$_2$CH$_2$—N(R$_3$)(R$_4$)(CH$_2$COO—)    (X)

wherein: $R_2$ is chosen from an alkyl radical derived from an acid $R_2$—COOH present in hydrolysed coconut oil, heptyl, nonyl, and undecyl radicals, $R_3$ is a β-hydroxyethyl group and $R_4$ is a carboxymethyl group; and

$R_5$—CONHCH$_2$CH$_2$—N(B)(C)    (XI)

wherein:
B is —CH$_2$CH$_2$OX', C is —(CH$_2$)$_z$—Y', with z=1 or 2,
X' is chosen from —CH$_2$CH$_2$—COOH and a hydrogen atom,
Y' is chosen from —COOH and a —CH$_2$—CHOH—SO$_3$H radical, and $R_5$ is chosen from an alkyl radical of an acid $R_9$—COOH present in coconut oil or in hydrolysed linseed oil, and alkyl radicals, for example, a $C_7$, $C_9$, $C_{11}$, and $C_{13}$ alkyl radical, and a $C_{17}$ alkyl radical and its iso form, and an unsaturated $C_{17}$ radical; and $R_9$ is chosen from alkyl radicals derived from flax and coco.

These compounds are classified in the CTFA dictionary, 5th edition, 1993, under the names disodium cocoamphodiacetate, disodium lauroamphodiacetate, disodium caprylamphodiacetate, disodium caprvloamphodiacetate, disodium cocoamphodipropionate, disodium lauroamphodipropionate, disodium caprylamphodipropionate, disodium caprvloamphodipropionate, lauroamphodipropionic acid, and cocoamphodipropionic acid.

By way of non-limiting example, mention may be made of the cocoamphodiacetate sold under the trade name MIRANOL C2M concentrated by the company Rhodia Chimie.

(iv) The cationic surfactants may be chosen from:

A) the quaternary ammonium salts of formula (XII):

(XII)

wherein X is an anion chosen from halides, such as chloride, bromide, and iodide, and ($C_2$-$C_6$)alkyl sulfates, for example, methyl sulfate, phosphates, alkyl, and alkylaryl sulfonates, and anions derived from organic acid, such as acetate or lactate, and a) the radicals $R_1$ to $R_3$, which may be identical or different, are chosen from $C_1$-$C_4$ linear and branched aliphatic radicals, and aromatic radicals, such as aryl, for example a phenyl radical, or alkylaryl. The aliphatic radicals can comprise heteroatoms such as oxygen, nitrogen, sulfur, and halogens. The aliphatic radicals are chosen, for example, from alkyl, alkoxy, and alkylamide radicals, $R_4$ is chosen from a $C_{16}$-$C_{30}$ linear and branched alkyl radical.

The cationic surfactant is, in at least one embodiment, a behenyltrimethylammonium salt, for example, chloride.

b) the radicals $R_1$ and $R_2$, which may be identical or different, are chosen from $C_1$-$C_4$ linear and branched aliphatic radicals, and aromatic radicals, such as aryl or alkylaryl. The aliphatic radicals can comprise heteroatoms such as oxygen, nitrogen, sulfur, and halogens. The aliphatic radicals are chosen, for example, from $C_1$-$C_4$ alkyl, alkoxy, alkylamide, and hydroxyalkyl radicals;

$R_3$ and $R_4$, which may be identical or different, are chosen from $C_{12}$-$C_{30}$ branched alkyl radicals, wherein the radicals comprise at least one ester or amide function.

$R_3$ and $R_4$ are chosen from ($C_{12}$-$C_{22}$)alkylamido($C_2$-$C_6$)alkyl and ($C_{12}$-$C_{22}$)alkylacetate radicals.

In at least one embodiment, the cationic surfactant is a stearamidopropyldimethyl(myristyl acetate)ammonium salt, for example, chloride.

B)—the quaternary ammonium salts of imidazolinium, such as formula (XIII):

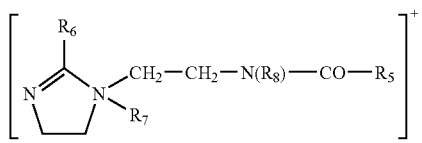

(XIII)

wherein $R_5$ is chosen from a $C_8$-$C_{30}$ alkenyl and alkyl radical, for example fatty acid derivatives of tallow, $R_6$ is chosen from a hydrogen atom, a $C_1$-$C_4$ alkyl radical, and a $C_8$-$C_{30}$ alkenyl and alkyl radical, $R_7$ is chosen from a $C_1$-$C_4$ alkyl radical, $R_8$ is chosen from a hydrogen atom and a $C_1$-$C_4$ alkyl radical, and X is an anion chosen from halides, phosphates, acetates, lactates, alkyl sulfates, alkyl sulfonates, and alkylaryl sulfonates. In one embodiment, $R_5$ and $R_6$ are a mixture of $C_{12}$-$C_{21}$ alkenyl and alkyl radicals, such as fatty acid derivatives of tallow, $R_7$ is methyl and $R_8$ is a hydrogen atom. Such a product is, for example, Quaternium-27 (CTFA 1997) or Quaternium-83 (CTFA 1997), which are sold under the names REWOQUAT W75, W90, W75PG, and W75HPG by the company Witco, C)— the diquaternary ammonium salts of formula (XIV):

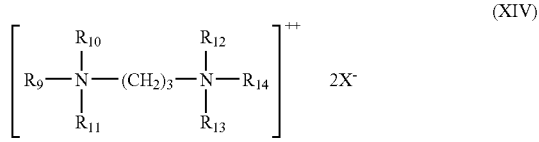

(XIV)

wherein $R_9$ is chosen from a $C_{16}$-$C_{30}$ aliphatic radical, $R_{10}$, $R_{11}$, $R_{12}$, $R_{13}$, and $R_{14}$, which may be identical or different, are chosen from hydrogen atoms and $C_1$-$C_4$ alkyl radicals, and X is an anion chosen from halides, acetates, phosphates, nitrates, and methyl sulfates. Such diquaternary ammonium salts comprise, for example, propanetallowediammonium dichloride;

D)—the quaternary ammonium salts comprising at least one ester function of formula (XV):

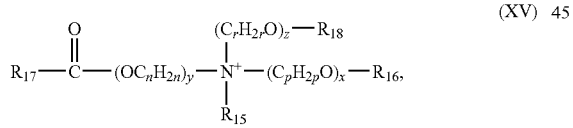

(XV)

wherein:

$R_{15}$ is chosen from a $C_1$-$C_6$ alkyl radical and a $C_1$-$C_6$ hydroxyalkyl, and a dihydroxyalkyl radical;

$R_{16}$ is chosen from:

a radical $R_{19}$

linear and branched, saturated and unsaturated $C_1$-$C_{22}$ hydrocarbon radicals $R_{20}$, and a hydrogen atom, $R_{18}$ is chosen from:

a radical $R_{21}$

linear and branched, saturated and unsaturated $C_1$-$C_6$ hydrocarbon radicals $R_{22}$, and a hydrogen atom, $R_{17}$, $R_{19}$, and $R_{21}$, which may be identical or different, are chosen from linear and branched, saturated and unsaturated $C_7$-$C_{21}$ hydrocarbon radicals;

n, p, and r, which may be identical or different, are integers ranging from 2 to 6;

y is an integer ranging from 1 to 10;

x and z, which may be identical or different, are integers ranging from 0 to 10; and $X^-$ is a simple or complex, organic or inorganic anion;

with the proviso that the sum x+y+z is from 1 to 15, that when x is 0, then $R_{16}$ is $R_{20}$, and that when z is 0, then $R_{18}$ is $R_{22}$.

Non-limiting mention may be made of the ammonium salts of formula (XV) wherein:

$R_{15}$ is a methyl or ethyl radical;

x and y are 1;

z is 0 or 1;

n, p, and r are 2;

$R_{16}$ is chosen from:

a radical $R_{19}$

methyl, ethyl, and $C_{14}$-$C_{22}$ hydrocarbon radicals, and a hydrogen atom;

$R_{17}$, $R_{19}$, and $R_{21}$, which may be identical or different, are chosen from linear and branched, saturated and unsaturated $C_7$-$C_{21}$ hydrocarbon radicals; and $R_{18}$ is chosen from:

a radical $R_{21}$

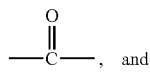

and a hydrogen atom.

Such compounds are sold, for example, under the names DEHYQUART by the company Cognis, STEPANQUAT by the company Stepan, NOXAMIUM by the company Ceca, and REWOQUAT WE 18 by the company Rewo-Witco.

Suitable quaternary ammonium salts include, but are not limited to behenyltrimethylammonium chloride and stearamidopropylmethyl(myristyl acetate)ammonium chloride, sold, for instance, under the name CERAPHYL 70 by the company Van Dyk, and Quaternium-27 or Quaternium-83 sold by the company Witco.

According to the compositions disclosed herein, mixtures of surfactants, for example, mixtures of anionic surfactants, mixtures of anionic surfactants and of amphoteric, cationic and nonionic surfactants, or mixtures of cationic surfactants with nonionic or amphoteric surfactants may be used. In at least one embodiment, a mixture comprising at least one anionic surfactant and at least one amphoteric surfactant may be used.

The compositions disclosed herein may also comprise at least one additive chosen from thickeners, antidandruff and anti-seborrhoeic agents, hair-loss counteractants, fragrances, nacreous agents, hydroxy acids, electrolytes, fatty acid esters, preserving agents, silicone and non-silicone sunscreens, vitamins, provitamins such as panthenol, anionic and nonionic polymers, proteins, protein hydrolysates, 18-methyl-eicosanoic acid, fluoro and perfluoro oils, fatty amines, fatty acids and derivatives thereof, fatty alcohols, and derivatives thereof, and also mixtures of these various compounds, and any other additive conventionally used in cosmetics that does not affect the properties of the compositions disclosed herein.

The compositions in accordance with the present disclosure may also comprise 0% to 5% of nacreous or opacifying agents that are well known in the prior art, such as sodium or magnesium palmitate, sodium or magnesium stearate or hydroxystearate, fatty-chain acyl derivatives such as ethylene glycol or polyethylene glycol monostearates or distearates, fatty-chain ethers such as distearyl ether and 1-(hexadecyloxy)-2-octadecanol, and fatty alcohols, such as stearyl alcohol, cetyl alcohol, behenyl alcohol, and mixtures thereof.

The at least one additive optionally present in the compositions disclosed herein, may be present in an amount ranging from 0.001% to 20% by weight, relative to the total weight of the composition. The precise amount of each additive is readily determined by a person skilled in the art on the basis of its nature and its function.

According to the present disclosure, the physiologically and cosmetically acceptable medium may consist solely of water or of a mixture of water and a cosmetically acceptable solvent such as a $C_1$-$C_4$ lower alcohol, for instance ethanol, isopropanol, tert-butanol or n-butanol; alkylene glycols, for instance propylene glycol, and glycol ethers.

In one embodiment, the composition comprises water in an amount ranging from 50% to 95% by weight, relative to the total weight of the composition, such as from 60 to 90% by weight.

The compositions according to the present disclosure have a final pH generally between 3 and 10, for example between 4 and 8. Adjusting the pH to the desired value may be performed conventionally by adding a base (organic or mineral base) to the composition, for example aqueous ammonia or a primary, secondary or tertiary (poly)amine, for instance monoethanolamine, diethanolamine, triethanolamine, isopropanolamine or 1,3-propanediamine, or by adding a mineral or organic acid, such as a carboxylic acid, for example, citric acid.

The compositions in accordance with the present disclosure may be used, for example, for washing or treating keratin materials such as the hair, the skin, the eyelashes, the eyebrows, the nails, the lips, and the scalp, and in at least one embodiment, the hair.

The compositions disclosed herein may be used as products, for instance for washing, caring for, conditioning, holding the hairstyle, and shaping keratin materials such as the hair.

In at least one embodiment, the compositions of the present disclosure may be in the form of shampoo, rinse-out or leave-in hair conditioner, compositions for permanent-waving, relaxing, dyeing or bleaching the hair, or in the form of compositions to be applied before or after dyeing, bleaching, permanent-waving, or relaxing the hair or else between the two steps of a permanent-waving or hair-relaxing operation.

In another embodiment, the compositions are washing and foaming compositions for the hair and/or the skin.

In at least one embodiment, the compositions are foaming detergent compositions such as shampoos, shower gels and bubble baths, or makeup-removing products. Such compositions comprise at least one detergent surfactant.

The at least one surfactant may then be chosen, by way of non-limiting example, from anionic, amphoteric, nonionic surfactants, and mixtures thereof.

When the compositions in accordance with the present disclosure are in the form of detergent compositions, such as shampoos, at least one anionic surfactant or mixtures of at least one anionic surfactant, at least one amphoteric surfactant, or of at least one nonionic surfactant is used.

In at least one embodiment, a mixture comprising at least one anionic surfactant and at least one amphoteric surfactant is used.

Use may be made, for example, of an anionic surfactant chosen from sodium, triethanolamine and ammonium ($C_{12}$-$C_{14}$)alkyl sulfates, sodium, triethanolamine or ammonium ($C_{12}$-$C_{14}$)alkyl ether sulfates oxyethylenated comprising 2.2 mol of ethylene oxide, sodium cocoyl isethionate and sodium α-($C_{14}$-$C_{16}$)olefin sulfonate, and mixtures thereof with:

either an amphoteric surfactant such as the amine derivatives known as disodium cocoamphodipropionate or sodium cocoamphopropionate sold, for instance, by the company Rhodia Chimie under the trade name MIRANOL C2M Conc. as an aqueous solution comprising 38% active material, or under the name MIRANOL C32;

or an amphoteric surfactant of zwitterionic type, such as alkylbetaines, for example the cocobetaine sold under the name DEHYTON AB 30 as an aqueous solution comprising 32% AM by the company Cognis, and the cocoamidopropylbetaine sold, for instance, by Goldschmidt under the name TEGOBETAINE F50.

The minimum quantity of surfactant is chosen in a sufficient amount in order to give the final composition satisfactory foaming power and/or detergent power.

Accordingly, the detergent surfactant may be present in an amount ranging from 3% to 30% by weight, for example from 6% to 25% by weight, and further for example from 8% to 20% by weight, relative to the total weight of the final composition.

The foaming power of the compositions disclosed herein, characterized by a foam height, is generally greater than 75 mm, such as greater than 100 mm, measured according to the modified Ross-Miles method (NF T 73-404/IS696).

The modifications to the method are the following:

The measurement is performed at a temperature of 22° C. with osmosed water. The concentration of the solution is 2 g/l. The height of the drop is 1 m. The amount of composition that is dropped is 200 ml. These 200 ml of composition fall into a measuring cylinder 50 mm in diameter and containing 50 ml of the test composition. The measurement is taken 5 minutes after stopping the flow of the composition.

In another embodiment, when the composition is in the form of a hair conditioner optionally to be rinsed out, it may further comprise at least one cationic surfactant, the concentration of the said surfactants may range from 0.1% to 10% by weight, such as from 0.5% to 5% by weight, relative to the total weight of the composition.

The compositions of the present disclosure may also be in the form of permanent-waving, hair-relaxing, dyeing, or bleaching compositions, or in the form of rinse-out compositions to be applied before or after dyeing, bleaching, permanent-waving, or relaxing the hair or alternatively between the two steps of a permanent-waving or hair-relaxing operation. The compositions disclosed herein may be in the form of aqueous or aqueous-alcoholic lotions for skincare and/or haircare, or in the form of a gel, a milk, a cream, an emulsion, a thickened lotion, or a mousse and may be used for the skin, the nails, the eyelashes, the lips, and such as the hair.

The compositions may be conditioned in various forms, for instance, in vaporizers, pump-dispenser bottles or in aerosol containers to allow an application of the composition in vaporized form or in the form of a mousse. Such conditioning forms are indicated, for example, when it is desired to obtain a spray, a lacquer, or a mousse for treating the hair.

Another aspect of the present disclosure is a process for treating keratin materials such as the skin or the hair, comprising applying to the keratin materials a cosmetic composition as defined above, and then optionally rinsing with water after an optional leave-in time.

Thus, this process according to the present disclosure allows holding of the hairstyle, and treatment, care and washing of or makeup removal from the skin, the hair or any other keratin material.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

In the examples, AM means active material.

EXAMPLE 1

A hair conditioner having the following composition, was prepared:

| | |
|---|---|
| Stearyl alcohol[1] | 2 g |
| Polyacrylate-1 crosspolymer as an emulsion at 20% (by weight) in water[2] (copolymer of acrylic or methacrylic acid esters, of di(C1-4 alkyl)amino(C1-6 alkyl) methacrylate, of PEG/PPG-30/5 allyl ether, of C10-30 PEG 20-25 alkyl ether methacrylate and of C2-6 hydroxyalkyl methacrylate crosslinked with ethylene glycol dimethacrylate) | 0.2 g AM |
| Polydimethyl/methyl aminoethyl aminopropyl siloxane as a nonionic microemulsion[3] | 0.8 g AM |
| Behenyltrimethylammonium chloride as a solution in a water/isopropanol mixture[4] | 1.58 g AM |
| Methyl alkyl alkylamidoethyl imidazolinium methosulfate as a solution in propylene glycol[5] | 2.5 g AM |
| Lactic acid | qs pH 4 |
| Chlorhexidine hydrochloride | 0.03 g |
| Methyl p-hydroxybenzoate | 0.3 g |
| Candelilla wax | 0.4 g |
| Fragrance | 0.4 g |
| Water | qs 100 g |

[1]sold under the trade name LANETTE 18 by the company Cognis
[2]sold under the trade name CARBOPOL Aqua CC Polymer by the company Noveon
[3]sold under the name SME253 by the company Momentive Performance Materials
[4]sold under the name GENAMIN KDMP by the company Clariant
[5]sold under the name VARISOFT W575 PG by the company Goldschmidt This composition was stable overtime and had a thick texture.

The composition gave the hair disentangling, suppleness, sheen, and smoothness.

EXAMPLE 2

A hair conditioner having the composition below was prepared:

| | |
|---|---|
| Stearyl alcohol[1] | 2 g |
| Polyacrylate-1 crosspolymer as an emulsion at 20% (by weight) in water[2] | 0.2 g AM |
| Polydimethylsiloxane comprising aminoethyl iminopropyl groups, as a nonionic microemulsion at 17% (by weight) in water[3] | 0.9 g AM |
| Behenyltrimethylammonium chloride as a solution in a water/isopropanol mixture[4] | 1.58 g AM |
| Methyl alkyl alkylamidoethyl imidazolinium methosulfate as a solution in propylene glycol[5] | 2.5 g AM |
| Lactic acid | qs pH 4 |
| Chlorhexidine hydrochloride | 0.03 g |
| Methyl p-hydroxybenzoate | 0.3 g |
| Candelilla wax | 0.4 g |
| Stearyl alcohol[1] | 2 g |
| Fragrance | 0.4 g |
| Water | qs 100 g |

[1]sold under the trade name LANETTE 18 by the company Cognis
[2]sold under the trade name CARBOPOL Aqua CC Polymer by the company Noveon
[3]sold under the name WACKER-BELSIL ADM LOG1 by the company Wacker
[4]sold under the name GENAMIN KDMP by the company Clariant
[5]sold under the name VARISOFT W575 PG by the company Goldschmidt This composition was stable over time and had a thick texture.

The composition gave the hair disentangling, suppleness, sheen and smoothness.

EXAMPLE 3

A shampoo composition was prepared:

| | |
|---|---|
| Sodium lauryl ether sulfate (2.2 EO) as an aqueous solution (TEXAPON AOS 225 UP from Cognis) | 12 g AM |
| Cocoylbetaine as an aqueous solution (DEHYTON AB 30 from Cognis) | 5 g AM |
| Lauryl ether carboxylic acid (4.5 EO) (AKYPO RLM 45 CA from Kao) | 0.9 g AM |
| Copolymer of acrylic or methacrylic acid esters, of di(C1-4 alkyl)amino(C1-6 alkyl) methacrylate, of PEG/PPG-30/5 allyl ether, of C10-30 PEG 20-25 alkyl ether methacrylate and of C2-6 hydroxyalkyl methacrylate crosslinked with ethylene glycol dimethacrylate, as an | 0.6 g AM |

| | |
|---|---|
| emulsion at 20% by weight in water (CARBOPOL Aqua CC Polymer from Noveon) | |
| Hydroxyethylcellulose quaternized with 2,3-epoxypropyl trimethylammonium chloride (JR 400 from Amerchol) | 0.6 g |
| Polydimethylsiloxane comprising aminoethyl and aminoisobutyl groups, with trimethylsiloxy end groups (DC 2-8566 Amino Fluid from Dow Corning) | 1 g |
| Preserving agents | 1.1 g |
| Mica-titanium dioxide-brown iron oxide | 0.005 g |
| Fragrance | 0.5 g |
| Polyethoxylated propylene glycol oleate (55 EO) and propylene glycol oleate as a water-glycol solution (ANTIL 141 from Goldschmidt) | <0.2 g AM |
| Citric acid or sodium hydroxide | qs pH 5.3 |
| Deionized water | qs 100 g |

This composition had a good texture that was stable over time. When applied to the hair, it gave sheen and smoothness.

EXAMPLE 4

A hair conditioner having the composition below was prepared:

| | |
|---|---|
| Stearyl alcohol[(1)] | 2 g |
| Polyacrylate-1 crosspolymer as an emulsion at 20% (by weight) in water[(2)] | 0.2 g AM |
| Quaternium-80 as a solution comprising 50% AM in propylene glycol (ABIL QUAT 3272 from Goldschmidt) | 0.375 g AM |
| Behenyltrimethylammonium chloride as a solution in a water/isopropanol mixture[(4)] | 1.58 g AM |
| Methyl alkyl alkylamidoethyl imidazolinium methosulfate as a solution in propylene glycol[(5)] | 2.5 g AM |
| Lactic acid | qs pH 4 |
| Chlorhexidine hydrochloride | 0.03 g |
| Methyl p-hydroxybenzoate | 0.3 g |
| Candelilla wax | 0.4 g |
| Stearyl alcohol[(1)] | 2 g |
| Fragrance | 0.4 g |
| Water | qs 100 g |

[(1)]sold under the trade name LANETTE 18 by the company Cognis
[(2)]sold under the trade name CARBOPOL Aqua CC Polymer by the company Noveon
[(4)]sold under the name GENAMIN KDMP by the company Clarian
[(5)]sold under the name VARISOFT W575 PG by the company Goldschmidt This composition was stable over time and had a thick texture. The composition gave the hair disentangling, suppleness, sheen and smoothness.

What is claimed is:

1. A cosmetic composition, comprising, in a cosmetically acceptable medium:
    (i)—at least one cationic polymer produced by polymerization of a monomer mixture comprising:
        a) at least one vinyl monomer substituted with at least one amino group chosen from:
            mono($C_1$-$C_4$)alkylamino($C_1$-$C_8$)alkyl(meth)acrylates,
            di($C_1$-$C_4$)alkylamino($C_1$-$C_8$)alkyl(meth)acrylates,
            mono($C_1$-$C_4$)alkylamino($C_1$-$C_8$)alkyl(meth)acrylamides,
            di($C_1$-$C_4$)alkylamino($C_1$-$C_8$)alkyl(meth)acrylamides,
            heterocyclic (meth)acrylamides comprising a nitrogen atom,
            heterocyclic (meth)acrylates comprising a nitrogen atom, and
            mixtures thereof,
        b) at least one hydrophobic nonionic vinyl monomer chosen from formulae (I) and (II):

$$CH_2=C(X)Z, \quad (I)$$

$$CH_2=CH-OC(O)R; \quad (II)$$

wherein:
X is chosen from a hydrogen atom and a methyl group;
Z is chosen from the groups —C(O)OR$^1$, —C(O)NH$_2$, —C(O)NHR$^1$, —C(O)N(R$^1$)$_2$, —C$_6$H$_5$, —C$_6$H$_4$R$^1$, —C$_6$H$_4$OR$^1$, —C$_6$H$_4$Cl, —CN, —NHC(O)CH$_3$, —NHC(O)H, N-(2-pyrrolidonyl), N-caprolactamyl, —C(O)NHC(CH$_3$)$_3$, —C(O)NHCH$_2$CH$_2$—NH—CH$_2$CH$_2$-urea, —Si(R)$_3$, —C(O)O(CH$_2$)$_x$Si(R)$_3$, —C(O)NH(CH$_2$)$_x$Si(R)$_3$, and —(CH$_2$)$_x$Si(R)$_3$;
x is an integer ranging from 1 to 6;
each R independently is a $C_1$-$C_{30}$ alkyl group;
each R$^1$ is independently chosen from a $C_1$-$C_{30}$ alkyl group, a $C_2$-$C_{30}$ hydroxyalkyl group, and a $C_1$-$C_{30}$ haloalkyl group;
    c) at least one associative vinyl monomer chosen from monomers of formula (III):

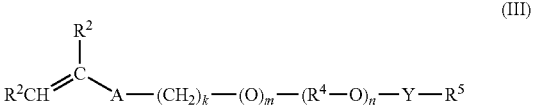

(III)

wherein:
each R$^2$ is independently chosen from a hydrogen atom, a methyl group, a —C(O)OH group, and a —C(O)OR$^3$ group;
R$^3$ is chosen from a $C_1$-$C_{30}$ alkyl;
A is chosen from —CH$_2$C(O)O—, —C(O)O—, —O—, CH$_2$O, —NHC(O)NH—, —C(O)NH—, —Ar—(CE$_2$)$_z$-NHC(O)O—, —Ar—(CE$_2$)$_z$-NHC(O)NH—, and —CH$_2$CH$_2$—NHC(O)—;
Ar is a divalent aryl group;
E is chosen from a hydrogen atom and a methyl group;
z is an integer ranging from 0 to 1;
k is an integer ranging from 0 to 30;
m is an integer ranging from 0 to 1,
with the proviso that when k is 0, then m is 0, and when k is an integer ranging from 1 to 30, then m is 1;
(R$^4$—O)$_n$ is a polyoxyalkylene, which is a homopolymer, a random copolymer, or a block copolymer, comprising $C_2$-$C_4$ oxyalkylene units;
R$^4$ is chosen from $C_2$H$_4$, $C_3$H$_6$, $C_4$H$_8$, and mixtures thereof;
n is an integer ranging from 5 to 250;

Y is chosen from —R⁴O—, —R⁴NH—, —C(O)—, —C(O)NH—, R⁴NHC(O)NH—, and —C(O)NHC(O)—;

R⁵ is chosen from a substituted and unsubstituted alkyl, a phenyl substituted with a $C_2$-$C_{40}$ alkyl group, a $C_2$-$C_{40}$ alkyl substituted with an aryl group, and a $C_8$-$C_{80}$ complex ester, wherein the alkyl group R⁵ optionally comprises at least one substituent chosen from hydroxyl, alkoxy, and halo groups;

d) at least one semi-hydrophobic vinyl surfactant monomer chosen from monomers of formulae (IV) and (V):

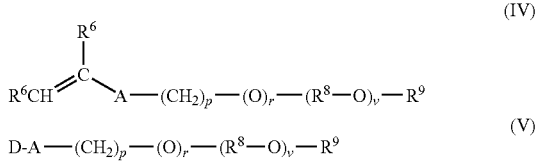

wherein:
each R⁶ is independently chosen from a hydrogen atom, a $C_1$-$C_{30}$ alkyl, —C(O)OH, and C(O)OR⁷;
R⁷ is a $C_1$-$C_{30}$ alkyl;
A is chosen from —CH₂C(O)O—, —C(O)O—, —O—, —CH₂O—, —NHC(O)NH—, —C(O)NH—, —Ar—(CE₂)$_z$-NHC(O)O—, —Ar—(CE₂)$_z$-NHC(O)NH—, and —CH₂CH₂—NHC(O)—;
Ar is a divalent aryl group;
E is chosen from a hydrogen atom and a methyl group;
z is an integer ranging from 0 to 1;
p is an integer ranging from 0 to 30;
r is an integer ranging from 0 to 1,
with the provisos that when p is 0, then r is 0, and when p is an integer ranging from 1 to 30, then r is 1;
(R⁸—O)$_v$ is a polyoxyalkylene, which is a homopolymer, a random copolymer, or a block copolymer, comprising $C_2$-$C_4$ oxyalkylene units, wherein R⁸ is chosen from $C_2H_4$, $C_3H_6$, $C_4H_8$, and mixtures thereof, and v is an integer ranging from 5 to 250;
R⁹ is chosen from a hydrogen atom and a $C_1$-$C_4$ alkyl group; and
D is chosen from a $C_8$-$C_{30}$ alkenyl group optionally substituted with a carboxyl group; and e) at least one hydroxylated nonionic vinyl monomer chosen from: P2 $C_1$-$C_6$ hydroxyalkyl(meth)acrylates, ($C_1$-$C_4$ hydroxyalkyl)(meth)acrylamides, and mixtures thereof, and (ii)—at least one amino silicone chosen from amino silicones comprising at least one primary amine function of formula (VI):

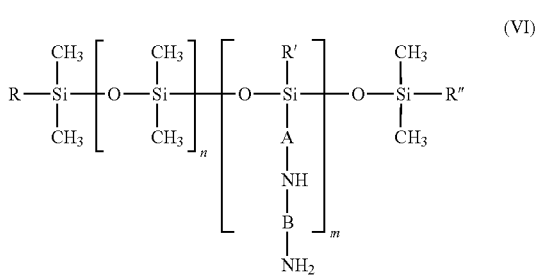

wherein R, R', and R'', which may be identical or different, are each independently chosen from $C_1$-$C_4$ alkyl radicals, $C_1$-$C_4$ alkoxy radicals and hydroxyl radicals; A and B are independently chosen from linear and branched $C_2$-$C_8$ alkylene radicals,
with the proviso that R and R'' are not simultaneously hydroxyl groups, and
m and n are integers that depend on the molecular weight and whose sum ranges from 1 to 2000.

2. The composition according to claim 1, wherein the at least one vinyl monomer substituted with at least one amino group is chosen from mono- or di($C_1$-$C_4$ alkyl)amino($C_1$-$C_4$ alkyl)(meth)acrylates; mono- or di($C_1$-$C_4$ alkyl)amino($C_1$-$C_4$ alkyl)(meth)acrylamides; (meth)acrylamides or (meth)acrylates with a heterocyclic group comprising a nitrogen atom; and nitrogenous heterocycles comprising at least one vinyl group.

3. The composition according to claim 1, wherein the at least one vinyl monomer substituted with at least one amino group is present in an amount ranging from 10% to 70% by weight, relative to the total weight of the monomer mixture.

4. The composition according to claim 1, wherein the at least one hydrophobic nonionic vinyl monomer is chosen from $C_1$-$C_{30}$ alkyl(meth)acrylates, ($C_1$-$C_{30}$ alkyl)(meth)acrylamides, styrene, substituted styrenes, vinyl esters, unsaturated nitriles, and unsaturated silanes.

5. The composition according to claim 1, wherein the at least one hydrophobic nonionic vinyl monomer is present in an amount ranging from 20% to 80% by weight, relative to the total weight of the monomer mixture.

6. The composition according to claim 1, wherein the at least one associative vinyl monomer is chosen from polyethoxylated cetyl(meth)acrylates, polyethoxylated cetearyl (meth)acrylates, polyethoxylated stearyl(meth)acrylates, polyethoxylated arachidyl (meth)acrylates, polyethoxylated behenyl(meth)acrylates, polyethoxylated lauryl (meth)acrylates, polyethoxylated cerotyl(meth)acrylates, polyethoxylated montanyl (meth)acrylates, polyethoxylated melissyl (meth)acrylates, polyethoxylated lacceryl (meth)acrylates, polyethoxylated 2,4,6-tris(1'-phenylethyl)phenyl(meth)acrylates, polyethoxylated hydrogenated castor oil (meth)acrylates, polyethoxylated canola (meth)acrylates, polyethoxylated cholesteryl(meth)acrylates, and mixtures thereof, wherein the polyethoxylated portion of the monomer comprises from 5 to 100 ethylene oxide units.

7. The composition according to claim 1, wherein the at least one associative vinyl monomer is present in an amount ranging from 0.001% to 25% by weight, relative to the weight of the monomer mixture.

8. The composition according to claim 1, wherein the monomer mixture comprises at least one semi-hydrophobic vinyl surfactant monomer of formulae:

$$CH_2=CH-O(CH_2)_aO(C_3H_6O)_b(C_2H_4-O)_cH \text{ or}$$

$$CH_2=CHCH_2O(C_3H_6O)_d(C_2H_4O)_eH;$$

wherein:
a is an integer ranging from 2 to 4;
b is an integer ranging from 1 to 10;
c is an integer ranging from 5 to 50;
d is an integer ranging from 1 to 10; and
e is an integer ranging from 5 to 50.

9. The composition according to claim 1, wherein the at least one semi-hydrophobic vinyl surfactant monomer is present in an amount ranging from 0.01% to 25% by weight, relative to the weight of the monomer mixture.

10. The composition according to claim 1, wherein the at least one hydroxylated nonionic vinyl monomer is 2-hydroxyethyl methacrylate.

11. The composition according to claim 1, wherein the at least one hydroxylated nonionic vinyl monomer is present in an amount ranging from 0.01% to 10% by weight, relative to the weight of the monomer mixture.

12. The composition according to claim 11, wherein the monomer mixture comprises, relative to the total weight of the monomer mixture:
   a) from 20% to 60% by weight of at least one vinyl monomer substituted with at least one amino group,
   b) from 20% to 70% by weight of at least one hydrophobic nonionic vinyl monomer,
   c) from 0.01% to 15% by weight of at least one associative vinyl monomer,
   d) from 0.1% to 10% by weight of at least one semi-hydrophobic vinyl surfactant monomer,
   e) from 0.01% to 10% by weight of at least one hydroxylated nonionic vinyl monomer,
   f) from 0.001°)/0 to 5% by weight of at least one crosslinking monomer,
   g) from 0.001% to 10% by weight of at least one chain-transfer agent, and
   h) from 0 to 2% by weight of at least one polymeric stabilizer.

13. The composition according to claim 1, wherein the monomer mixture comprises:
   a di($C_1$-$C_4$ alkyl)amino($C_1$-$C_6$ alkyl)methacrylate,
   at least one $C_1$-$C_{30}$ alkyl ester of (meth)acrylic acid,
   a $C_{10}$-$C_{30}$ alkyl methacrylate polyethoxylated comprising from 20 to 30 mol of ethylene oxide,
   a 30/5 polyethylene glycol/polypropylene glycol allyl ether,
   a hydroxy($C_2$-$C_6$ alkyl)methacrylate, and
   an ethylene glycol dimethacrylate.

14. The composition according to claim 1, wherein the at least one cationic polymer (i) is present in an amount ranging from 0.01% to 10% by weight, relative to the total weight of the composition.

15. The composition according to claim 1, wherein the at least one amino silicone ii) has the formula (VI):

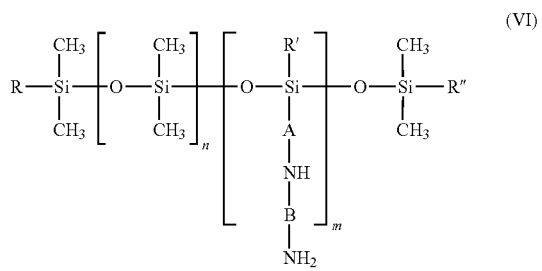

wherein:
R, R', and R", which may be identical or different, are chosen from $C_1$-$C_4$ alkoxy and hydroxyl radicals, and wherein at least one of the radicals R and R" is an alkoxy radical.

16. The composition according to claim 1, wherein the amino silicone of formula (VI) is the silicone corresponding to formula (VII):

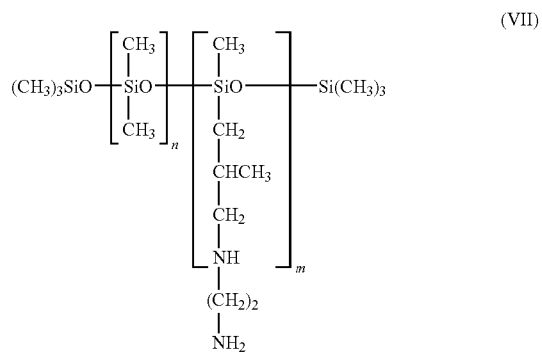

wherein m and n are integers which are dependent on the molecular weight, and whose sum ranges from 1 to 2000.

17. The composition according to claim 1, wherein the at least one amino silicone (ii) is present in a concentration of between 0.001% and 20% by weight, relative to the total weight of the composition.

18. The composition according to claim 1, further comprising at least one non-amino silicone.

19. The composition according to claim 18, wherein the different additional non-amino silicones are present in an amount ranging from 0.001% and 20% by weight, relative to the total weight of the composition.

20. The composition according to claim 1, further comprising at least one agent beneficial to keratin materials, chosen from esters of $C_1$-$C_{30}$ carboxylic acids, $C_1$-$C_{30}$ mono-hydroxylated or polyhydroxylated alcohols, plant, animal, mineral, or synthetic oils, waxes, ceramides, pseudoceramides, and cationic polymers.

21. The composition according to claim 1, wherein the composition is in the form of a foaming detergent composition.

22. The composition according to claim 1, wherein the composition is in the form of a rinse-out or leave-in hair-conditioning composition.

23. A process for treating keratin materials, comprising applying to keratin materials a cosmetic composition comprising, in a cosmetically acceptable medium:
   (i)—at least one cationic polymer produced by polymerization of a monomer mixture comprising:
      a) at least one vinyl monomer substituted with at least one amino group, chosen from:
         mono($C_1$-$C_4$)alkylamino($C_1$-$C_8$)alkyl(meth)acrylates,
         di($C_1$-$C_4$)alkylamino($C_1$-$C_8$)alkyl(meth)acrylates,
         mono($C_1$-$C_4$)alkylamino($C_1$-$C_8$)alkyl(meth)acrylamides,
         di($C_1$-$C_4$)alkylamino($C_1$-$C_8$)alkyl(meth)acrylamides,
         heterocyclic (meth)acrylamides comprising a nitrogen atom,
         heterocyclic (meth)acrylates comprising a nitrogen atom, and mixtures thereof,
      b) at least one hydrophobic nonionic vinyl monomer chosen from formulae (I) and (II):

$$CH_2=C(X)Z, \tag{I}$$

$$CH_2=CH-OC(O)R; \tag{II}$$

wherein:
X is chosen from a hydrogen atom and a methyl group;
Z is chosen from the groups —C(O)OR$^1$, —C(O)NH$_2$, —C(O)NHR$^1$, —C(O)N(R$^1$)$_2$, —C$_6$H$_5$, —C$_6$H$_4$R$^1$, —$C_6H_4OR^1$, —$C_6H_4Cl$, —CN, —$NHC(O)CH_3$, —NHC(O)H, N-(2-pyrrolidonyl), N-caprolactamyl, —$C(O)NHC(CH_3)_3$, —$C(O)NHCH_2CH_2$—NH—$CH_2CH_2$-urea, —$Si(R)_3$, —$C(O)O(CH_2)_xSi(R)_3$, —$C(O)NH(CH_2)_xSi(R)_3$, and —$(CH_2)_xSi(R)_3$;

x is an integer ranging from 1 to 6;

each R independently is a $C_1$-$C_{30}$ alkyl group;

each $R^1$ is independently chosen from a $C_1$-$C_{30}$ alkyl group, a $C_2$-$C_{30}$ hydroxyalkyl group, and a $C_1$-$C_{30}$ haloalkyl group;

c) at least one associative vinyl monomer chosen from monomers of formula (III):

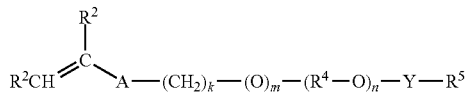

(III)

wherein:

each $R^2$ is independently chosen from a hydrogen atom, a methyl group, a —C(O)OH group, and a —C(O)OR$^3$ group;

$R^3$ is chosen from a $C_1$-$C_{30}$ alkyl;

A is chosen from —$CH_2C(O)O$—, —$C(O)O$—, —O—, $CH_2O$, —NHC(O)NH—, —C(O)NH—, —Ar—$(CE_2)_z$-NHC(O)O—, —Ar—$(CE_2)_z$-NHC(O)NH—, and —$CH_2CH_2$—NHC(O)—;

Ar is a divalent aryl group;

E is chosen from a hydrogen atom and a methyl group;

z is an integer ranging from 0 to 1;

k is an integer ranging from 0 to 30;

m is an integer ranging from 0 to 1, with the proviso that when k is 0, then m is 0, and when k is an integer ranging from 1 to 30, then m is 1;

$(R^4$—$O)_n$ is a polyoxyalkylene, which is a homopolymer, a random copolymer, or a block copolymer, comprising $C_2$-$C_4$ oxyalkylene units;

$R^4$ is chosen from $C_2H_4$, $C_3H_6$, $C_4H_8$, and mixtures thereof;

n is an integer ranging from 5 to 250;

Y is chosen from —$R^4O$—, —$R^4NH$—, —C(O)—, —C(O)NH—, $R^4NHC(O)NH$—, and —C(O)NHC(O)—;

$R^5$ is chosen from a substituted and unsubstituted alkyl, a phenyl substituted with a $C_2$-$C_{40}$ alkyl group, a $C_2$-$C_{40}$ alkyl substituted with an aryl group, and a $C_8$-$C_{80}$ complex ester, wherein the alkyl group $R^5$ optionally comprises at least one substituent chosen from hydroxyl, alkoxy, and halo groups;

d) at least one semi-hydrophobic vinyl surfactant monomer chosen from monomers of formulae (IV) and (V):

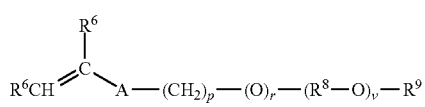

(IV)

(V)

wherein:

each $R^6$ is independently chosen from a hydrogen atom, a $C_1$-$C_{30}$ alkyl, —C(O)OH, and $C(O)OR^7$;

$R^7$ is a $C_1$-$C_{30}$ alkyl;

A is chosen from —$CH_2C(O)O$—, —$C(O)O$—, —O—, —$CH_2O$, —NHC(O)NH—, —C(O)NH—, —Ar—$(CE_2)_z$-NHC(O)O—, —Ar—$(CE_2)_z$-NHC(O)NH—, and —$CH_2CH_2$—NHC(O)—;

Ar is a divalent aryl group;

E is chosen from a hydrogen atom and a methyl group;

z is an integer ranging from 0 to 1;

p is an integer ranging from 0 to 30;

r is an integer ranging from 0 to 1, with the provisos that when p is 0, then r is 0, and when p is an integer ranging from 1 to 30, then r is 1;

$(R^8$—$O)_v$ is a polyoxyalkylene, which is a homopolymer, a random copolymer, or a block copolymer, comprising $C_2$-$C_4$ oxyalkylene units, wherein $R^8$ is chosen from $C_2H_4$, $C_3H_6$, $C_4H_8$, and mixtures thereof, and v is an integer ranging from 5 to 250;

$R^9$ is chosen from a hydrogen atom and a $C_1$-$C_4$ alkyl group; and

D is chosen from a $C_8$-$C_{30}$ alkenyl group optionally substituted with a carboxyl group; and e) at least one hydroxylated nonionic vinyl monomer chosen from:

$C_1$-$C_6$ hydroxyalkyl(meth)acrylates, ($C_1$-$C_4$ hydroxyalkyl)(meth)acrylamides, and mixtures thereof, and (ii)—at least one amino silicone chosen from amino silicones comprising at least one primary amine function of formula (VI):

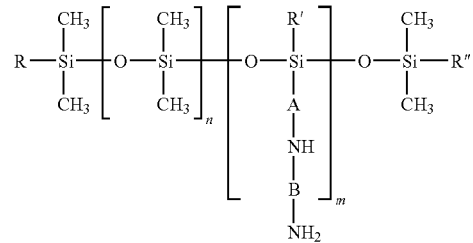

(VI)

wherein R, R', and R", which may be identical or different, are each independently chosen from $C_1$-$C_4$ alkyl radicals, $C_1$-$C_4$ alkoxy radicals and hydroxyl radicals; A and B are independently chosen from linear and branched $C_2$-$C_8$ alkylene radicals, with the proviso that R and R" are not simultaneously hydroxyl groups, and m and n are integers that depend on the molecular weight and whose sum ranges from 1 to 2000, optionally followed by rinsing with water, after an optional leave-in time.

* * * * *

UNITED STATES PATENT AND TRADEMARK OFFICE
CERTIFICATE OF CORRECTION

PATENT NO. : 8,846,017 B2  
APPLICATION NO. : 12/210642  
DATED : September 30, 2014  
INVENTOR(S) : Olga Biganska et al.

Page 1 of 1

It is certified that error appears in the above-identified patent and that said Letters Patent is hereby corrected as shown below:

In the Claims

Col. 31, claim 1, line 47, after "from:" delete "P2".

Col. 33, claim 12, line 20, change "0.001 °)/0" to -- 0.001 % --.

Signed and Sealed this
Eighth Day of September, 2015

Michelle K. Lee
*Director of the United States Patent and Trademark Office*